United States Patent
Yoshida et al.

(10) Patent No.: US 6,940,092 B2
(45) Date of Patent: Sep. 6, 2005

(54) ELECTRICALLY CONDUCTING ORGANIC COMPOUND AND ELECTRONIC DEVICE

(75) Inventors: Hiroaki Yoshida, Kawasaki (JP); Wataru Sotoyama, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 10/107,450

(22) Filed: Mar. 28, 2002

(65) Prior Publication Data

US 2003/0089904 A1 May 15, 2003

(30) Foreign Application Priority Data

Oct. 15, 2001 (JP) ........................................ 2001-317095

(51) Int. Cl.$^7$ .............................................. H01L 35/24
(52) U.S. Cl. ................ 257/40; 252/301.16; 252/301.36
(58) Field of Search .............. 257/40, 313; 252/301.16, 252/301.36, 299.01

(56) References Cited

U.S. PATENT DOCUMENTS

| | | | | |
|---|---|---|---|---|
| 4,281,053 A | * | 7/1981 | Tang .......................... 430/59.1 |
| 5,142,343 A | * | 8/1992 | Hosokawa et al. .......... 257/103 |
| 5,155,566 A | * | 10/1992 | Nakayama et al. ........... 257/40 |
| 5,190,633 A | * | 3/1993 | Fetzer et al. .................. 208/99 |
| 5,232,577 A | * | 8/1993 | Fetzer et al. .................. 208/96 |
| 5,336,546 A | * | 8/1994 | Hironaka et al. ........... 428/209 |
| 5,534,375 A | * | 7/1996 | Kaneko et al. .......... 430/58.75 |
| 5,936,259 A | * | 8/1999 | Katz et al. .................... 257/40 |
| 6,071,670 A | * | 6/2000 | Ushirogouchi et al. .. 430/270.1 |
| 6,248,884 B1 | * | 6/2001 | Lam et al. ..................... 544/59 |
| 6,358,633 B1 | * | 3/2002 | Sano et al. .................. 428/690 |
| 6,481,217 B1 | * | 11/2002 | Okazaki et al. .............. 62/46.1 |
| 6,593,977 B2 | * | 7/2003 | Ishihara et al. ............... 349/43 |
| 6,621,098 B1 | * | 9/2003 | Jackson et al. ............... 257/40 |
| 6,753,097 B2 | * | 6/2004 | Toguchi et al. ............. 428/690 |
| 2002/0098441 A1 | * | 7/2002 | Okino et al. ............. 430/270.1 |

FOREIGN PATENT DOCUMENTS

JP          2002216963          *     8/2002          ........... H05B/33/14

* cited by examiner

*Primary Examiner*—Long Pham
*Assistant Examiner*—Thao X. Le
(74) *Attorney, Agent, or Firm*—Arent Fox PLLC

(57) ABSTRACT

An electrically conducting organic compound comprising a condensed polycyclic aromatic compound containing from 8 to 14 condensed rings and being solubilized in a solvent by the introduction of a functional group into any condensed ring of the compound. The electrically conducting organic compound is used as a constituent element in the production of electronic devices.

12 Claims, 12 Drawing Sheets

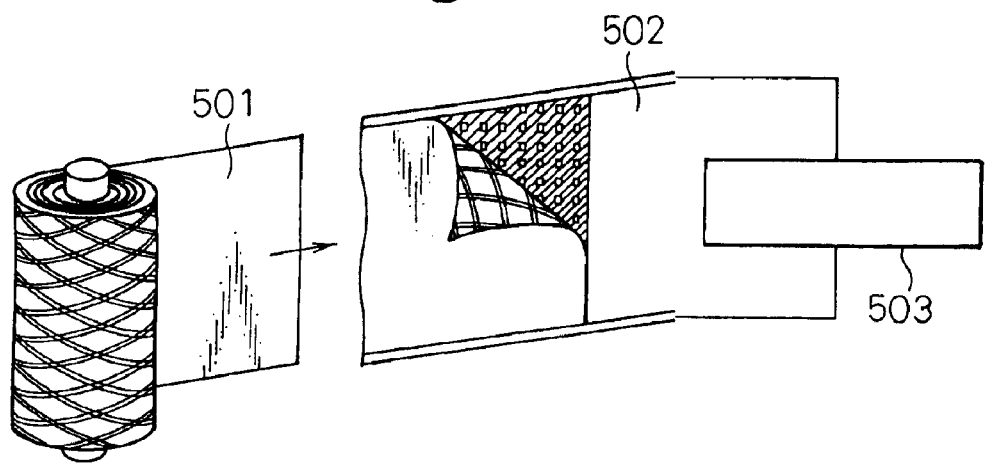
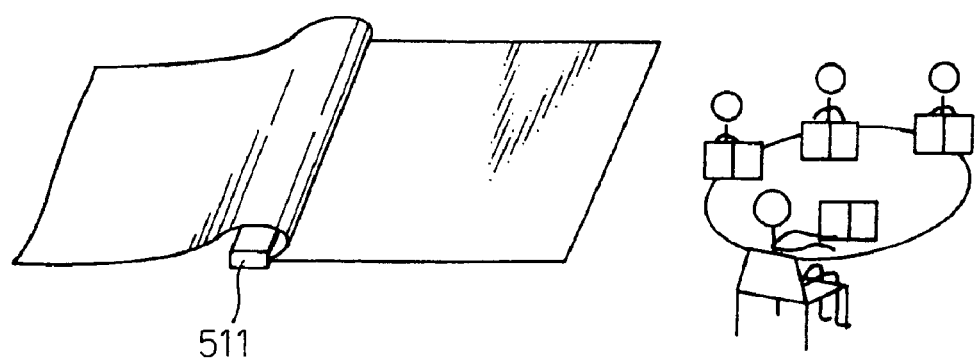

ELECTRICALLY CONDUCTING ORGANIC COMPOUND AND ELECTRONIC DEVICE

CROSS-REFERENCE TO RELATED APPLICATIONS

This application is based upon and claims a priority of Japanese Patent Application No. 2001-317095, filed Oct. 15, 2001, the contents being incorporated herein by reference.

BACKGROUND OF THE INVENTION

1. Field of the Invention

The present invention relates to an electrically conducting organic compound and, more specifically, the present invention relates to an organic semiconductor which can be used in the production of electronic devices such as transistors, particularly to an organic semiconductor applicable to flexible electronic devices such as electronic paper. The present invention also relates to electronic devices using this organic semiconductor.

2. Description of the Related Art

In the field of electronic display, liquid crystal displays and organic EL displays are improving in their performance and also making rapid progress toward higher precision and larger size. On the other hand, a display showing excellent portability by having, like paper, both good visibility and flexibility, namely, a flexible property capable of changing a shape by fold-bending, a so-called electronic paper, is keenly demanded. To realise this electronic paper, it is essential that a thin film transistor can be formed on a plastic substrate or, in other words, a flexible circuit for driving a picture element can be realized. However, currently existing electronic circuits mainly comprising an inorganic material such as polycrystalline silicon or amorphous silicon require a large-scale process such as high temperature and high vacuum and, taking account of the heat resistance and high production cost of the plastic substrate, these circuits are applicable, at best, to only a part of an instrument and cannot be used widely in practice. In order to solve these problems, attention is being focused on an organic semiconductor having excellent flexibility, requiring no high-temperature/vacuum process, such as vapor deposition, and allowing an inexpensive printing means to be applied.

The means for the film formation of an organic semiconductor are roughly classified into vacuum process, such as vapor deposition, and spin coating, casting or printing from a solution. In the case of applying an organic semiconductor to a device such as field effect transistor, the vapor deposition method capable of ensuring good crystallinity in molecule has been heretofore predominantly used so as to achieve as high a carrier mobility as possible. As for representative organic semiconductors formed by the vapor deposition method, oligothiophene (see, H. Akimichi et al., *Applied Physics Letters*, 58(14), Apr. 8, 1991), pentacene (see, C. D. Dimitrakopoulos et al., *Applied Physics Letters*, 80(4), Aug. 15, 1996), copper phthalocyanine and the like have been reported. On the other hand, as for representative organic semiconductors formed by casting, spin coating or printing from a solution, polythienylene vinylene (see, H. Fuchigami et al., *Applied Physics Letters*, 63(10), Sep. 6, 1993), polyalkylthiophene (see, A. Tsumura et al., *Applied Physics Letters*, Vol. 49, P. 1210 (1986), and *Journal American Chemical Society*, vol. 117, p. 233 (1995)) and the like have been reported. In addition, a film formation example where the LB (Langmuir-Blodgett) method is applied for forming a single molecular film or controlling the orientation property of molecule with an attempt to bring out a new function, has been also reported (see, J. Paloheimo et al., *Applied Physics Letters*, 56(12), Mar. 19, 1990). The method for calculating the field effect mobility of these molecules is described in detail in these publications.

Incidentally, in the case of using such an organic semiconductor as the channel layer of a field effect transistor, its field effect mobility is approximately from 0.1 to 0.01 $cm^2/Vs$ and this is about several figures lower than that of an amorphous silicon semiconductor (up to 1 $cm^2/Vs$) even in a vapor deposition system which is reported to give a high mobility. In the case of forming the film from a solution, the field effect mobility is usually further lower, by about 1 or 2 figures, due to the difficulty in controlling the molecular orientation. In other words, a most important problem in realizing an organic semiconductor is how high field effect mobility can be achieved by a simple and easy production process. To have high mobility, the organic semiconductor generally must have a π-conjugate system largely extended within the molecule and furthermore, the organic semiconductor molecule must be oriented in the conductive direction. The oligothiophene, polythiophene and poly(p-phenylene vinylene) referred to above are a linear electrically conducting polymer where the π-conjugate system runs along the main chain. On the other hand, the material system where the π-conjugate system is planarly extended includes condensed polycyclic aromatic molecules such as ovalene, coronene and bianthrene. With respect to conventionally known means for controlling the orientation of organic semiconductor molecules, Japanese Unexamined Patent Publication (Kokai) No. 9-83040 discloses a technique of coating a π-conjugate polymer, such as polythiophene, on an orientation film substrate subjected to a rubbing treatment, or orienting the molecules on an orientation film by introducing a liquid crystalline substituent as a side chain or by applying an external force such as magnetic field or electric field.

However, the orientation force on an organic semiconductor by the orientation film is weak and, at present, a sufficiently high molecular orientation cannot be attained. The introduction of a crystalline substituent incurs a problem such that the conduction path of the charge carrier is decreased due to the presence of the substituent not contributing to the electrical conductivity and the mobility is rather reduced. The organic semiconductor where the π-conjugate system is planarly extended, such as pentacene, phthalocyanine and ovalene, has almost no solubility in a solvent and since the film is formed by vapor deposition, the cost is a great problem.

SUMMARY OF THE INVENTION

The present invention is directed to solve the above problems in prior art techniques, and an object of the present invention is to provide an electrically conducting organic compound which can exhibit a high field effect mobility and at the same time, can be produced by a simple and easy process at a low cost.

Another object of the present invention is to provide an electrically conducting organic compound useful for the production of electronic devices such as electronic paper.

Still another object of the present invention is to provide a high-performance electronic device having flexibility.

These objects and other objects of the present invention will be appreciated from the preferred embodiments described hereinafter.

In one aspect, the present invention resides in an electrically conducting organic compound comprising a condensed polycyclic aromatic compound containing from 8 to 14 condensed rings, and being solubilized in a solvent by introducing a functional group into any condensed ring of the aromatic compound.

In another aspect, the present invention resides in an electronic device characterized by having a structure comprising, as a member thereof, a constituent element formed of the electrically conducting organic compound of the present invention.

Preferably, the electronic device of the present invention is a sheet-form display device comprising a sheet-form display functional layer and at least one layer containing a constituent element for allowing the sheet-form display functional layer to function, wherein the constituent element comprises the electrically conducting organic compound of the present invention. The sheet-form display device includes various forms but a typical example thereof is electronic paper.

As described in detail below, accordingly to the present invention, a side chain substituent such as an alkyl group is introduced as a functional group into a condensed polycyclic aromatic compound in which the π-conjugate system is planarly extended and which has high mobility, such as ovalene, whereby good solubility in a solvent can be ensured and an electronic device having desired properties can be manufactured without impairing the high field effect mobility even by an easy process of forming a thin film from a solution system, such as casting or printing. Furthermore, by imparting a functionality to the functional group itself introduced into the condensed polycyclic aromatic compound, the molecules can be oriented at the time of coating and drying the aromatic compound. For example, by introducing a functional group having liquid crystallinity or a long-chain alkyl group, a desired molecular orientation can be attained.

BRIEF DESCRIPTION OF THE DRAWINGS

FIG. 9 is a view for explaining an electronic wallpaper system as one embodiment of the sheet-form display device of the present invention;

FIG. 10 is a view for explaining an electronic conference document as one embodiment of the sheet-form display device of the present invention;

DESCRIPTION OF THE PREFERRED EMBODIMENTS

Figure 1:
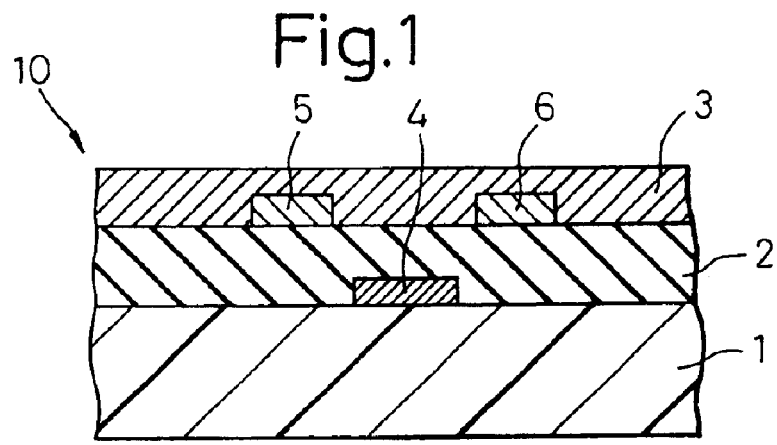
FIG. 1 is a cross-sectional view showing one construction example of the electrically conducting thin film transistor of the present invention.

The electrically conducting organic compound and the electronic device according to the present invention each can be advantageously practiced in various embodiments.

As described above, the electrically conducting organic compound of the present invention is a condensed polycyclic aromatic compound. In this aromatic compound, a functional group is introduced as a side chain into a condensed ring and thereby the compound is solubilized in a solvent. Examples of the functional group which is suitably used for this purpose include, but are not limited to, an alkyl group such as methyl group, ethyl group, butyl group and hexyl group; an aryl group such as phenyl group; an ether group such as polyethylene oxide group; an alkoxy group such as methoxy group, ethoxy group and propoxy group; a liquid crystal group such as mesogene group; a silane group such as permethyloligosilane group, perethyloligosilane group, permethylpolysilane group and perethylpolysilane group; and a combination or a composite material of these groups. This functional group may be substituted, if desired, or may be variously modified insofar as the effect of the present invention is not hindered, such that the aromatic compound is solubilized in a solvent without lowering the mobility thereof. Examples of the solvent as used herein include, but are not limited to, toluene, xylene, acetonitrile, tetrahydrofuran, chloroform and ethanol. Accordingly, the condensed polycyclic aromatic compound of the present invention may be dissolved in this solvent to a predetermined concentration to provide a coating solution, coated on a substrate or the like by a coating method such as casting, dip coating or spin coating, or by a printing method such as screen printing, and then cured. This film formation method can be performed simply and easily at a low cost as compared with conventional vapor deposition method and the like.

The condensed polycyclic aromatic compound of the present invention must have a molecular weight large enough to ensure the solubility in a solvent by the introduction of a side chain. Accordingly, the number of condensed rings contained is suitably from about 8 to 14. In other words, the condensed polycyclic aromatic compound usually has a molecular weight of preferably from about 350 to 2,000, more preferably from 350 to 1,000. Of course, insofar as a desired activity effect can be provided, the aromatic compound may have a number of condensed rings or a molecular weight other than those described above. If the number of condensed rings contained is less than 8, the electrical conduction of the π-conjugate system lowers and the mobility disadvantageously decreases, whereas if it exceeds 14, there may arise a problem such as abrupt decrease of the solubility in a solvent even if a functional group is introduced.

The condensed polycyclic aromatic compound of the present invention includes various aromatic compounds satisfying the above-described requirements. In particular, the compounds in which usefulness has been discovered by the present inventors are an ovalene derivative represented by the following formula (I):

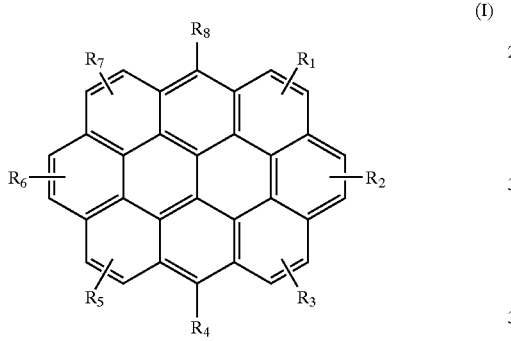

(I)

wherein $R_1$ to $R_8$, which may be the same or different, each represents a hydrogen atom or an arbitrary substituent, provided that at least two of $R_1$ to $R_8$ are an alkyl group, an aryl group, an ether group or a silane group; or a bianthrene derivative represented by the following formula (II):

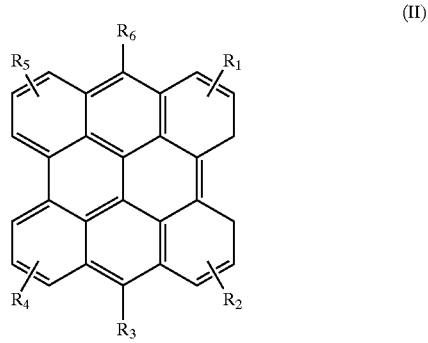

(II)

wherein $R_1$ to $R_6$, which may be the same or different, each represents a hydrogen atom or an arbitrary substituent, provided that at least two of $R_1$ to $R_6$ are an alkyl group, an aryl group, an ether group or a silane group. If desired, these aromatic compounds may be used in combination.

Typical examples of these ovalene derivative and bianthrene derivative can be represented, for example, by the following formulae:

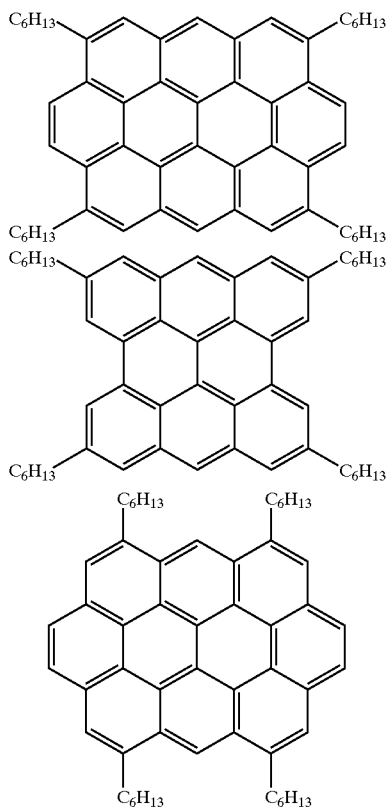

The condensed polycyclic aromatic compound of the present invention has a high field effect mobility and the field effect mobility calculated according to the method described in the publications described above is usually from about 0.001 to 0.03 cm$^2$/Vs. If the field effect mobility is less than 0.001 cm$^2$/Vs, there arises a problem such that the response speed of the electronic device is very slow.

The condensed polycyclic aromatic compound of the present invention can be advantageously prepared using a synthetic method commonly used for the production of compounds such as ovalene and bianthrene. At this time, the functional group for solubilizing the compound in a solvent can be introduced in accordance with a general method of adding a substituent to an aromatic ring. For example, in the case of introducing a hexyl group (—C$_6$H$_{13}$) into an aromatic ring of ovalene, the hydrogen atom in the periphery of the aromatic ring of ovalene is replaced by a chlorine atom (Cl) and, then, the chlorine atom is reacted with C$_6$H$_{13}$MgBr, whereby a hexyl group can be easily introduced.

The condensed polycyclic aromatic compound of the present invention can be advantageously used as one constituent element in various electronic devices by making good use of its excellent properties such as high mobility, appropriate orientation force and flexibility. The term "constituent element" as used herein means parts and units constituting the electronic device such as display device and the like of the present invention and is sometimes called "an element". Examples of the constituent element include, but are not limited to, various elements, including a power source element, such as a driving circuit, a control circuit, a communication circuit and an acoustic signal conversion element. It is also possible that the display functional element is the constituent element.

Typical examples of the sheet-form display device as a typical example of the electric device include the following devices, however, the sheet-form display device of the present invention is not limited thereto.

(1) A sheet-form display device characterized in that the device is constructed by an integrally molded sheet-form display functional layer and a sheet-form power source layer, the sheet-form display functional layer has one pair of opposing electrode plates with at least one electrode plate being transparent and performs a predetermined display operation by causing changes in the optical absorption or the optical reflection property, and the sheet-form power source layer supplies to the display functional layer an electric power necessary for driving the layer.

(2) The sheet-form display device as described in (1) above, wherein the display element for use in the sheet-form display functional layer is an electrophoretic display element which performs a predetermined display operation by enclosing a dispersion system containing electrophoretic particles into a space between one pair of opposing electrode plates with at least one electrode plate being transparent, changing the distribution state of the electrophoretic particles within the dispersion system under the action of a display control voltage applied between the electrodes, and thereby causing changes in the optical absorption or optical reflection property.

(3) The sheet-form display device as described in (1) above, wherein the display element for use in the sheet-form display functional layer is a microcapsule inversion-type display element which performs a predetermined display operation by enclosing colored particulate microcapsules capable of inversion according to the direction of an electric field applied into a space between one pair of opposing electrode plates with at least one electrode plate being transparent, changing the orientation direction of the microcapsules under the action of a display control voltage applied between the electrodes, and thereby causing changes in the optical absorption or optical reflection property.

(4) The sheet-form display device as described in (1) above, wherein the display element for use in the sheet-form display functional layer is a polymer dispersion-type liquid crystal element obtained by providing micropores on a polymer substance and enclosing a liquid crystal compound in the micropores.

(5) The sheet-form display device as described in (1) above, wherein the display element for use in the sheet-form display functional layer is an element capable of providing an electroluminescence phenomenon by causing changes in the optical absorption or optical reflection property under the action of an electric current passing through between one pair of opposing electrode plates with at least one electrode plate being transparent.

(6) The sheet-form display device as described in (1) above, wherein the display element for use in the sheet-form display functional layer is an element capable of providing an electrochromism phenomenon by causing changes in the optical absorption or optical reflection property under the action of an electric current passing through between one pair of opposing electrode plates with at least one electrode plate being transparent.

(7) A sheet-form display device characterized in that the device is constructed by integrally molded sheet-form display functional layer and sheet-form power source layer, the sheet-form display functional layer has one electrode plate and performs a predetermined display operation by causing changes in the optical absorption or optical reflection property under the action of an electric field applied between the electrode plate and a predetermined writing electrode or an electric current passing through between those two electrodes, and the sheet-form power source layer supplies to the display functional layer an electric power necessary for driving the layer.

(8) The sheet-form display device as described in (7) above, wherein the display element for use in the sheet-form display functional layer is an electrophoretic display element which has one electrode plate and a dispersion system capable of electrophoresis under the action of an electric field applied between the electrode plate and a predetermined writing electrode and which performs a predetermined display operation by changing the distribution state of the electrophoretic particles within the dispersion system under the action of a display control voltage applied between those two electrodes and thereby causing changes in the optical absorption or optical reflection property.

(9) The sheet-form display device as described in (7) above, wherein the display element for use in the sheet-form display functional layer is a microcapsule inversion-type display element which has one electrode plate and performs a predetermined display operation by enclosing colored particulate microcapsules capable of inversion according to an electric field applied into a space between the electrode plate and a predetermined writing electrode, changing the orientation direction of the microcapsules under the action of a display control voltage applied between those two electrodes, and thereby causing changes in the optical absorption or optical reflection property.

(10) The sheet-form display device as described in (7) above, wherein the display element for use in the sheet-form display functional layer is an element capable of providing an electrochromism phenomenon by causing changes in the optical absorption or optical reflection property according to an electric current passed through between the electrode plate and a predetermined writing electrode.

(11) The sheet-form display device as described in (1) or (7) above, wherein the display element for use in the sheet-form display functional layer is a magnetic display element.

(12) The sheet-form display device as described in (1) or (7) above, wherein the power source element for use in the sheet-form power source layer is a sheet-form primary battery having a pair of electrodes capable of allowing an irreversible oxidation reduction reaction to proceed, with the electrodes being connected by a sheet-form electrolyte.

(13) The sheet-form display device as described in (1) or (7) above, wherein the power source element for use in the sheet-form power source layer is a sheet-form secondary battery having a pair of electrodes capable of allowing a reversible oxidation reduction reaction to proceed, with the electrodes being connected by a sheet-form electrolyte.

(14) The sheet-form display device as described in (1) or (7) above, wherein the power source element for use in the sheet-form power source layer is a sheet-form photocell (or solar battery) capable of generating an electric power upon irradiation by light.

(15) The sheet-form display device as described in (1) or (7) above, wherein the power source element for use in the sheet-form power source layer is a sheet-form thermoelectromotive battery capable of converting the difference in heat directly into an electric power.

(16) The sheet-form display device as described in (1) or (7) above, wherein the power source element for use in the sheet-form power source layer is a sheet-form capacitor element having a pair of electrodes and being formed by bonding these two electrodes with a dielectric material or an electrolyte.

(17) A sheet-form display device constructed by integrally molding (a) a sheet-form display functional layer, (b) a sheet-form power source layer and (c) a layer for both or one of a driving circuit and a control circuit.

(18) A sheet-form display device having a display function and a communication function, which is constructed by integrally molding (a) a sheet-form display functional layer, (b) a sheet-form power source layer and (c) a layer for a communication circuit and both or one of a driving circuit and a control circuit.

(19) The sheet-form display device as described in (18) above, wherein the communication circuit is a circuit using an electromagnetic wave energy, a light energy or an acoustic energy as the transfer means.

(20) A sheet-form display device having a display function and an acoustic conversion function, which is constructed by integrally molding (a) a sheet-form display functional layer, (b) a sheet-form power source layer and (c) an acoustic signal conversion element layer capable of converting an acoustic signal into an electric signal, converting an electric signal into an acoustic signal or performing these two conversions.

(21) A sheet-form display device having a display function and an acoustic conversion function, which is constructed by integrally molding (a) a sheet-form display functional layer, (b) a sheet-form power source layer, (c) an acoustic signal conversion element layer capable of converting an acoustic signal into an electric signal, converting an electric signal into an acoustic signal or performing these two conversions, and (d) a layer for both or one of a driving circuit and a control circuit.

(22) A sheet-form display device having a display function and an acoustic conversion function, which is constructed by integrally molding (a) a sheet-form display functional layer, (b) a sheet-form power source layer, (c) an acoustic signal conversion element layer capable of converting an acoustic signal into an electric signal, converting an electric signal into an acoustic signal or performing these two conversions, and (d) a layer for a communication circuit and both or one of a driving circuit and a control circuit.

(23) A sheet-form display device constructed by integrally molding (a) a sheet-form display functional layer, and (b) a layer for at least one of a driving circuit, a control circuit and a communication circuit.

(24) A sheet-form display device comprising at least (a) a sheet-form display element and (b) an element for external connection. In one example, this sheet-form display device can display the information from an electronic or electric instrument by inserting an electrode terminal (may be designed to withdraw outside from the sheet-form display device on use) provided on the end face of the sheet-form display element into the connection means (e.g., slot) provided on the exterior electronic-electric instrument to connect with an electrode terminal within the slot. In this case, the necessary elements such as driving circuit and control circuit may be all or partially provided in the sheet-form display device side or in the side of instrument to which the device is connected.

(25) A sheet-form display device added with an input function by providing an input element as the data input means in any of the above-described sheet-form display devices. Examples of the data input element include a so-called touch sensor-type keyboard. This can be integrated into, for example, a part of a display element.

Examples of the electronic device which can be suitably used in the practice of the present invention include, but are not limited to, an organic thin film transistor such as a FET (field effect transistor). The organic thin film transistor of the present invention can be advantageously realized particularly in the form of a so-called electronic paper. Other than the organic thin film transistor, examples of the electronic device include a diode.

This is described more specifically. FIG. 1 is a view schematically showing an organic thin film transistor 10 as one example of the electronic device according to the present invention. This organic thin film transistor 10 can be manufactured, for example, as follows.

On a substrate 1 made of a flexible plastic material such as polyethersulfone (PES) or polyethylene terephthalate (PET), a gate electrode 4 is formed by appropriate means such as sputtering of gold or etching. Thereafter, on the surface of the substrate 1 with the gate electrode 4, an organic material having a high dielectric constant, such as polyacrylonitrile, polyvinylidene fluoride or cyanoethylated pullulan, is coated and cured to form a gate insulating film 2. If desired, the gate insulating film 2 may be subjected to an orientation treatment to impart a function as an orientation film or an orientation film (not shown) may be further formed on the gate insulating film 2. In this case, examples of the orientation film formed on the gate insulating film include, but are not limited to, a polyimide film subjected to a rubbing treatment, a polyimide film irradiated with a polarized ultraviolet ray, and a polyimide or polyvinyl cinnamate film polymerized to orient the molecules toward a specific direction using a polarized ultraviolet ray. Subsequently, on this gate insulating film 2, a source electrode 5 and a drain electrode 6 are disposed to provide a transistor substrate. Here, the gate, source and drain electrode materials of the transistor each may be any material insofar as it does not adversely affect the function of the transistor obtained. For example, in addition to the above-described metals such as gold, an inorganic compound material or an electrically conducting polymer material, such as indium tin oxide (ITO) or tin oxide ($SnO_2$), can be used as the electrode material.

After manufacturing a transistor substrate as such, the electrically conducting organic compound according to the present invention is dissolved in an appropriate solvent such as toluene and the obtained coating solution is coated on the transistor substrate by a casting method, a dip coating method or a spin coating method, and cured. Then, a channel layer 3 is formed as shown in the Figure. The thickness of the channel layer 3 varies depending on the kind of the transistor but is generally from about 10 to 500 nm. In place of coating, the coating solution of the electrically conducting organic compound may be printed by printing or the like. For example, the coating solution may also be printed only on the selected portion of the substrate using a mask by applying a screen printing method. Furthermore, a printing process comprising the steps of temporarily attaching the solution to a rubber disc or the like and then transferring it to a predetermined position on the substrate may also be used. For the purpose of preventing the intermingling of impurities or the permeation of moisture into the channel layer 3 formed, a protective layer such as moisture-proof film may be provided insofar as it does not inhibit the activity of the transistor.

The organic thin film transistor 10 produced through such a series of production processes can contribute to the reduction in the cost because the amount of electric current passing between the source electrode and the drain electrode can be modulated by the gate voltage and a high field effect mobility equal to that in conventional organic semiconductor compounds formed by vapor evaporation can be achieved by coating or printing of a solution. Furthermore, although the substrate used here for the purpose of explanation is a flexible plastic substrate, same effects can be obtained also in the case of an Si substrate or other non-flexible substrates. Accordingly, the electrically conducting organic compound of the present invention can be applied not only to a field effect transistor produced on a plastic substrate but also to other electronic devices where high field effect mobility and reduction of the cost by a simple and easy process are required.

The electronic device of the present invention includes various sheet-form display devices. These display devices are manufactured such that a display element, which has been heretofore dealt with as an independent element, is integrated with various elements including a power source element for allowing the display element to function, such as a driving circuit, a control circuit, a communication circuit and an acoustic conversion element, whereby the space factor can be improved and formation of the display part to have a large area and also ultrathin formation of the display device itself can be realized.

In the present invention, for obtaining such a specific sheet-form display device, each element is formed using a printing technique and a laminating technique which are advantageous in producing these elements in the sheet form.

Figure 2:
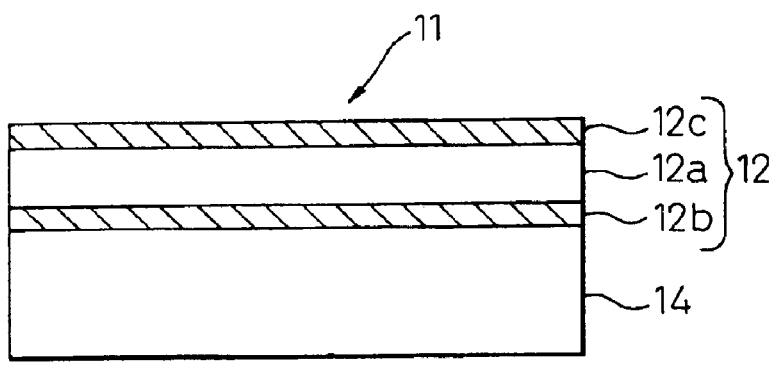
FIG. 2 is a schematic view of the sheet-form display device in a fundamental embodiment of the present invention.

For example, the display device 11 schematically shown in FIG. 2 according to a fundamental embodiment of the present invention comprises a display functional layer 12 and a power source layer 14 which are both in a sheet form. The display functional layer 12 can be formed from various sheet-form elements capable of exerting a display function based on various principles. In the display device 11 shown, the display functional layer 12 is composed of a display layer 12a and a pair of electrodes 12b and 12c sandwiching the display layer. For the display functional layer 12, the electrically conducting organic compound of the present invention can be used.

In the case of a sheet-form display device comprising a combination of an electrophoretic display element and a power source element, a display device where a sheet-form display element and a sheet-form power source element are integrated can be manufactured as follows. A microcapsule having enclosed therein electrophoretic particles is printed on a flexible substrate such as transparent electrode vapor deposited polyester using a technique such as screen printing, roller printing, ink jet printing and electrophotography and then, combined with a counter electrode, one part electrode material of the power source element is coated on the back surface of the substrate, an electrolyte sheet is placed thereon, a sheet having coated thereon another part electrode material is further attached thereon, and these members are subjected to a lamination process.

Other than the above-described display element applying the principle of electrophoresis, a display element according to an arbitrary display method applying a principle suitable for the formation of a sheet-form display may be employed, such as a display element applying the rotation of a colored microcapsule by an electric field, a so-called polymer dispersion-type liquid crystal element where a liquid crystal is stuffed into micropores provided on a polymer material, a display element applying the electrochromism or electroluminescence, and a display element according to a magnetic recording system of moving fine particles having magnetism by the control of the magnetism.

For example, the electrochromic display (ECD) as a display element applying the electrochromism is an element which utilizes the light absorptivity (absorbance) varying by the oxidation or reduction reaction and displays this variation as a change in color.

Such an element is composed of an electrochromic thin film, a display electrode, a counter electrode and an electrolyte and, when the electrochromic thin film formed on the display electrode is oxidized or reduced according to the electric potential of the display electrode, a change in color is seen.

At least either one of the display electrode and the counter electrode is a transparent electrode and the change in color of the electrochromic thin film can be observed from the outside.

For the transparent electrode, an electrically conducting polymer thin film such as tin oxide, tin-doped indium oxide or polyaniline can be used.

For the electrochromic thin film, the electrically conducting organic compound of the present invention can be used.

For the electrolyte, a liquid electrolyte obtained by dissolving a lithium salt such as $LiClO_4$, $LiBF_4$, $LiPF_6$, $LiCF_3SO_3$ in a nonaqueous solvent such as propylene carbonate, acetonitrile or γ-butyrolactone, or a so-called solid electrolyte obtained by adding a resin such as acrylonitrile or polyethylene oxide to a solvent such as lithium salt and propylene carbonate and forming the mixture into a semisolid or solid state through melting under heat, cooling and curing with a crosslinking agent can be used.

The electroluminescent (EL) device, as a display device applying electroluminescence, is a generic term for completely solid devices which self-emit light upon passage of an electric current. Heretofore, inorganic EL devices such as ZnS/Mn have been developed, however, these have a problem in that the driving voltage is as high as about 100 V and a sufficiently high luminance cannot be obtained. On the other hand, in recent years, development of organic electroluminescent (organic EL) devices suitable for thin-type displays has proceeded. The organic EL device emits light by itself, has excellent visibility, can respond quickly, can be made lightweight and thin, and can be driven at a low voltage of several volts or less. Therefore, its application to an inexpensive large-area full color flat panel display is expected and studies are being made thereon at present (see, *Nikkei Electronics,* page 99, Jan. 29, 1996).

The organic EL device in general has an operation principle close to the operation principle of light emitting diode (LED) and uses a light emitting layer (an organic semiconductor thin film having an ability of emitting fluorescent light), a carrier transporting layer and a pair of counter electrodes sandwiching those layers. The light emission phenomenon is based on the principle that when an electric field is applied between two electrodes, an electron is injected from the cathode, a hole is injected from the anode, and the recombination of electrons and holes in the light emitting layer causes a return of the energy level, from the conduction band to the valence electron band, while releasing the generated energy difference as light energy.

For each of the light emitting layer and the carrier transporting layer, a π electron organic semiconductor substance is generally used. For the light emitting layer substance, the electrically conducting organic compound of the present invention is used. For the hole transporting layer as the carrier transporting layer, a triphenylamine derivative (TAD) or the like is used and for the electron transporting layer, an oxadiazole derivative (PBD) or the like is used.

From the standpoint for seeking variety in the emission color and the long-term storage stability of the light emitting layer, substrates over a wide range are used for the light emitting layer and even a light emitting layer using a system of an amorphous polymer medium mixed with a fluorescent dye molecule or using a polymer alone such as poly-p-phenylene derivative (PPV) have been proposed.

The light emitting layer and the carrier (hole and electron) transporting layers disposed in both sides of the light emitting layer are interposed between the cathode electrode as an electron injecting electrode and the anode electrode for injecting holes, thereby constructing a laminate body.

The laminate body constructed by the above-described layers is usually disposed on a substrate.

The substrate is a support of the EL device and a transparent substrate such as glass or plastic is generally used. Preferred examples of the plastic include polyethylene terephthalate, polycarbonate, polymethyl methacrylate, polysulfone, polybutene, polymethyl pentene and the like.

On the substrate, a transparent electrode is provided as the anode electrode. For the transparent electrode material, an indium tin oxide (ITO) thin film or a tin oxide film can be used. Also, a metal having a large work function, such as aluminum or gold, or an electrically conducting polymer such as polyaniline, poly(3-methylthiophene) or polypyrrole may be used. The electrically conducting organic compound of the present invention may also be used.

As for the method for manufacturing the anode electrode, a vacuum deposition method or a sputtering method may be used. However, in the case of an electrically conducting polymer, a film can be formed directly on the substrate by using a soluble electrically conducting polymer, by coating a mixed solution with an appropriate binder resin on the substrate or by the electrolytic polymerization. The film thickness of the anode electrode is selected to give a visible light transmittance of 60% or more, preferably 80% or more, and in this case, the film thickness is generally from 10 to 1,000 nm, preferably from 20 to 500 nm.

The film thickness of the light emitting layer is usually from 10 to 200 nm, preferably from 20 to 80 nm. As for the organic light emitting substance used in this light emitting layer, a compound having a high fluorescent quantum yield, a high electron injection yield from the cathode electrode and a high electron mobility is effective. An oxyquinoline-based complex such as 8-hydroxyquinoline-aluminum complex ($AlQ_3$) is used and a diphenyl anthracene-based compound, a naphthostyryl-based pigment (NSD), a coumarin derivative, a pyran derivative or a rubrene-based compound is contained.

For the cathode electrode, various metal materials can be used and Mg, Li, Ca and alloys thereof, each having a small work function, are preferred. Examples thereof include a magnesium-aluminum alloy, a magnesium-silver alloy, a magnesium-indium alloy, an aluminum-lithium alloy and aluminum. In the present invention, when a power source layer is combined, it is preferred that this cathode electrode material can be used in common as the electrode materials for the battery.

As for the electron transporting substance between the light emitting layer and the cathode electrode layer, a substance having a large electron affinity and a high electron mobility is necessary. Examples of the substances which can be used include cyclopentadiene derivatives, bis-styrylbenzene derivatives, oxadiazole derivatives, triazole derivatives, p-phenylene compounds or polymers, and phenanthroline derivatives.

On the other hand, as for the hole transporting material between the light emitting layer and the anode electrode layer, a material having a low injection barrier from the anode electrode and having a high hole mobility is used. Examples of the material which can be used include aromatic diamine-based compounds such as N,N'-diphenyl-N,N'-bis(3-methylphenyl)-1,1'-biphenyl-4,4'-diamine (TPD) and 1,1'-bis(4-di-p-tolylaminophenyl)cyclohexane, hydrazone compounds, and tetraphenylbutadiene compounds. Also, polymer materials such as poly-N-vinylcarbazole and polysilane may be used.

Figure 3:
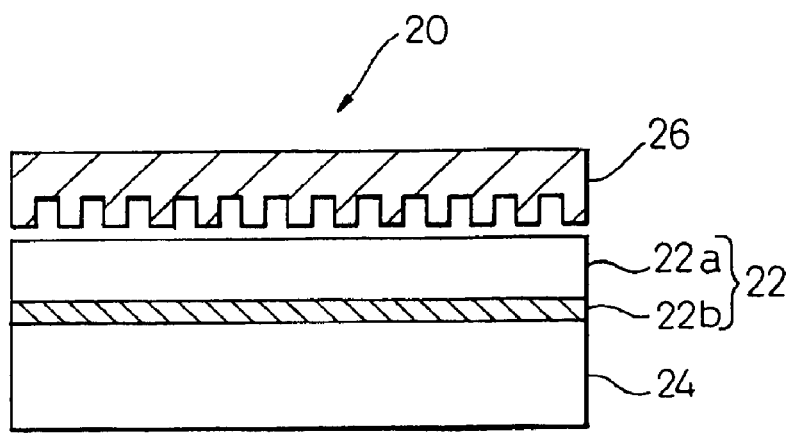
FIG. 3 is a view schematically showing the sheet-form display device in another embodiment of the present invention.

In the case of a display element of electrophoresis type, microcapsule inversion type or electrochromism type, it may be possible to provide only one electrode sheet in the display element of the display device and rewrite the display information in the display element by applying an electric field from an external writing electrode or by passing an electric current. FIG. 3 schematically shows a sheet-form display device according to this embodiment. In this Figure, 20 is a sheet-form display device, where 22 is a display functional layer composed here of a display layer 22a and an electrode 22b, and a writing electrode 26 is disposed in the side opposing the electrode 22b. Further, in the sheet-form display device 20, 24 is a power source layer. In this case, a writing device such as printer or hand scanner is necessary outside the display device.

In the present invention, various display elements can be used, however, on taking account of flexibility or foldability of the display device manufactured using that display element, a display element of a type where rotary balls (spherical rotators) or electrophoretic particles are contained in a microcapsule is more preferred.

Examples of the power source element which can be used include those belonging to a so-called primary battery species using, as the electrode material, zinc/graphite, manganese dioxide or lithium/manganese dioxide, or zinc/air; those belonging to a secondary battery species using, as the electrode material, nickel cadmium- or lithium-occludable carbon/lithium-occludable metal oxide, or lithium metal/electrically conducting polymer; those belonging to single crystal silicon or amorphous silicon species, polysilicon species, or solar battery species such as organic pigment type and inorganic pigment type; those belonging to a thermoelectric conversion battery species utilizing the Seebeck effect; and those belonging to capacitors such as electrolytic capacitor and electrical double layer capacitor. Among these, in the species of a primary battery, a secondary battery and a capacitor utilizing an electrochemical reaction, a so-called solid electrolyte obtained by solidifying an electrolyte is preferably used.

In the sheet-form display device of the present invention, a layer containing a circuit necessary for driving and controlling the display element may be integrally incorporated in addition to the display functional layer and the power source layer. In this case, the layer containing such a circuit must be a layer of not impairing the flexibility of the device.

Specific embodiments of the sheet-form display device according to the present invention are described below, however, the present invention is, of course, not limited to the following embodiments.

(1) Electronic Newspaper which Receives Information via Internet, Satellite Broadcast, etc. and Displays only the Desired Information and Which Can be Read Even when Folded in a Free Form; Foldable Electronic Book and Magazine; and Electronic Catalogue having Additionally Input Means Capable of Making Order for Commodities:

(1-1) Electronic Newspaper:

Examples of Form:

From tabloid to newspaper size, thin like paper, and foldable.

Examples of Function:

Receiving, data memory, switchover of picture plane, enlargement/reduction of displayed information, etc.

Examples of Constituent Element:

Display part, driving circuit, power source, communication (receiving) circuit, control circuit, memory, touch key, etc.

Figure 4:
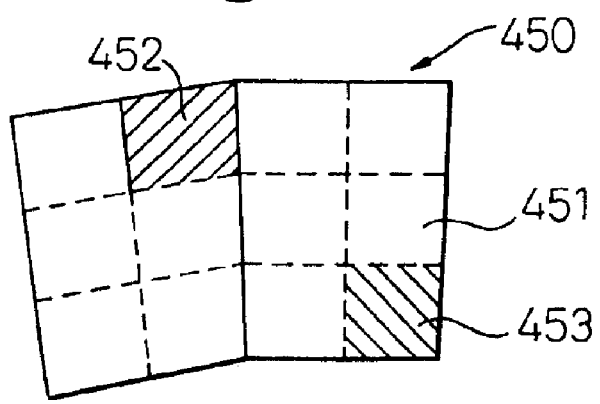
FIG. 4 is a view for explaining an electronic newspaper as one embodiment of the sheet-form display device of the present invention.

Examples of Application:

FIG. 4 shows the appearance. Via an antenna line (not shown) provided in the periphery of the display part 451 in a newspaper size, a newest article is received at a predetermined time and stored in the memory. A nominated article of higher priority is displayed at a predetermined position. The layer exclusive of the display layer, which is slightly inferior in the flexibility and foldability, is provided in a minimum size for folding of the electronic newspaper 450 at a designated position (slashed area 452 in the Figure) and other parts can be freely folded. When the newspaper is folded at predetermined positions shown by the broken lines in the Figure, it can be compactly folded to a minimum size. Since the displayed information is held even in the folded state, the article can be seen like a newspaper. In a part of the display plane (another slashed area 453 in the Figure), a transparent thin layer as a touch input key for performing a switch operation by the change or the like in the electrostatic capacitance or resistance value is provided and by this key operation, the information stored in the memory can be sequentially displayed.

(1-2) Electronic Book and Magazine

Examples of Form:

From small book to large magazine size, and thin like paper, a plurality of sheets can be bound at one end and can be turned or rolled up.

Examples of Function:

Receiving, data memory, switchover of picture plane, enlargement/reduction, automatic renewal of picture plane in agreement with turning, selection of page, input of memo.

Examples of Constituent Element:

Display part, driving circuit, power source, communication (receiving) circuit, control circuit, memory, input means, cover, etc.

Figure 5:
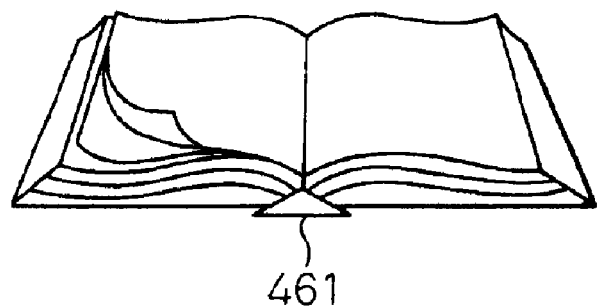
FIG. 5 is a view for explaining an electronic book as one embodiment of the sheet-form display device of the present invention.

Examples of Application:

FIG. 5 shows the appearance. A plurality of sheets are bound at the back cover 461 and an electronic circuit or an electronic part is housed in this part to enable use of even parts inferior in the shape variance. The display is made on the both surfaces of the display layer and the page can be turned like a book. When turned to the final page, the sensor inside the back cover perceives the action of turning back to the first page and the following page is automatically renewed and displayed. A touch key may also be provided on the back or front paper surface, so that, in addition to the control of reception and display, the switchover of display can be controlled by the key input. Furthermore, a touch position sensor may be provided throughout the display plane, so that a handwritten letter or illustration can be input as the digital information into the display plane utilizing the writing pressure of a pen or using an electronic pen to which an electric field or the like can be applied, and the digital information can be stored in the display and memory. Such information as a memo is associated with the page information of a book or the like and setting of an automatic display of the page can also be attained.

(1-3) Electronic Catalogue Additionally having Input Means

Examples of Function:

Receiving and sending, data memory, switchover of picture plane, enlargement/reduction, input, etc.

Examples of Constituent Element:

Display part, driving circuit, power source, communication (sending and receiving) circuit, control circuit, memory, input means, cover, etc.

Figure 6:
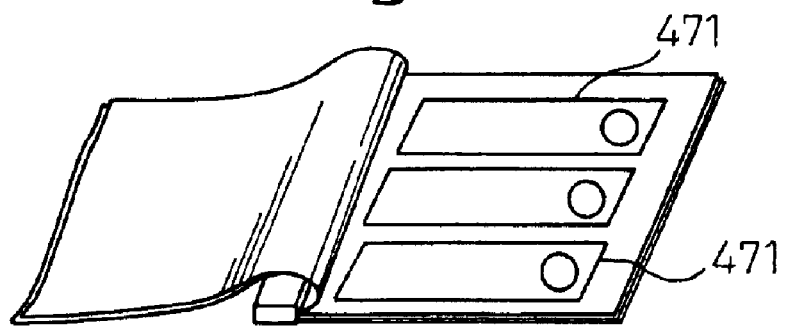
FIG. 6 is a view for explaining an electronic catalogue as one embodiment of the sheet-form display device of the present invention.

Examples of Application:

FIG. 6 shows the appearance. This device has an input means for the inputting by a touch key or an electronic pen and the information of commodity 471 is displayed. The necessary field is previously registered and after receiving renewal notification by communication, the commodity information is automatically renewed. The information from commodity list to detail can be displayed by switching over the picture plane. Based on the personal information input as a default by the communication function, an order can be made by one switching operation and an electronic account can be settled from the registered account. Other than the registered field, various commodities can be searched for and displayed and can be ordered.

(2) Display Board (Electronic Circulating Notice) System Capable of Attaching or Detaching to Wall and Automatically Receiving and Renewing Regional Information:

Examples of Form:

From A4 to A3 size (foldable into A4 size), slightly foldable board, and attachable/detachable to wall, etc.

Examples of Function:

Receiving and sending, data memory, switchover of picture plane, enlargement/reduction, input, individualization of parts (constituent element), signal display, etc.

Examples of Constituent Element:

Display part, driving circuit, power source, communication (sending and receiving) circuit, control circuit, memory, input means, signal display means, etc.

Figure 7A:
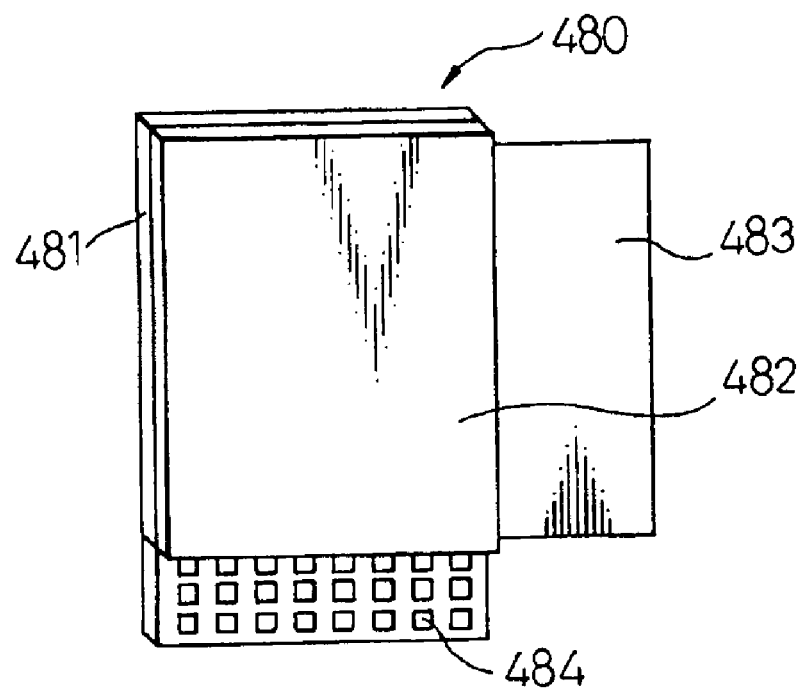
FIGS. 7A and 7B are views for explaining a display board system as one embodiment of the sheet-form display device of the present invention.
Figure 7B:
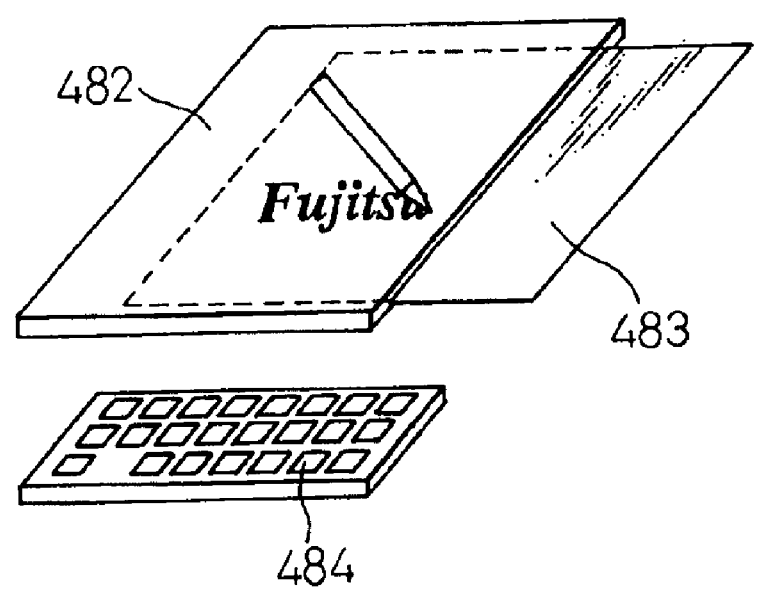

Examples of Application:

FIGS. 7A and 7B show the appearance of a display board system 480. A system having respective means for terminal connection, receiving and sending, data memory, switchover of picture plane, enlargement/reduction and input is provided on a wall. In the portion 481 fixed to the wall, a communication circuit and signal means (not shown) is provided, a display and input part 482 having provided therein a driving circuit, a control circuit, a power source and the like is removably fixed there, and a paper-like display device 483 is set in the display and the input part 482. The information is automatically renewed and the renewal of data is informed by the signal means (which generates a signal such as light or sound) provided in the system. The device additionally has input means 484 such as key pad or electronic pen. The input information can be confirmed and sent at the display part in whichever state the input means 484 is fixed to the wall or removed therefrom. Only the display element 483 can be removed and carried. In this case, information is displayed and held without power supply. In the display and input part 482, input by the key operation or hand writing can be made on a desk or the like even in the state removed from the wall. The interchange of data among respective departments separated into individual sites can be performed through the electrode, communication means or the like provided at the terminal part of each department.

(3) Communication tool for enabling to call partner only by operation of button (having input function) displayed on picture plane, to make conversation while seeing partner on picture plane and to send information input from picture plane as it is to partner:

Examples of Form:

From A4 to A3 size (foldable into A4 size), thin like paper at least in the display part, can be folded or rolled up.

Examples of Function:

Receiving and sending, data memory, switchover of picture plane, enlargement/reduction, inputting, sound, input of image, etc.

Examples of Constituent Element:

Display part, driving circuit, power source, communication (sending and receiving) circuit, control circuit, memory, input means, voice input and output means, image input and output means, etc.

Figure 8A:
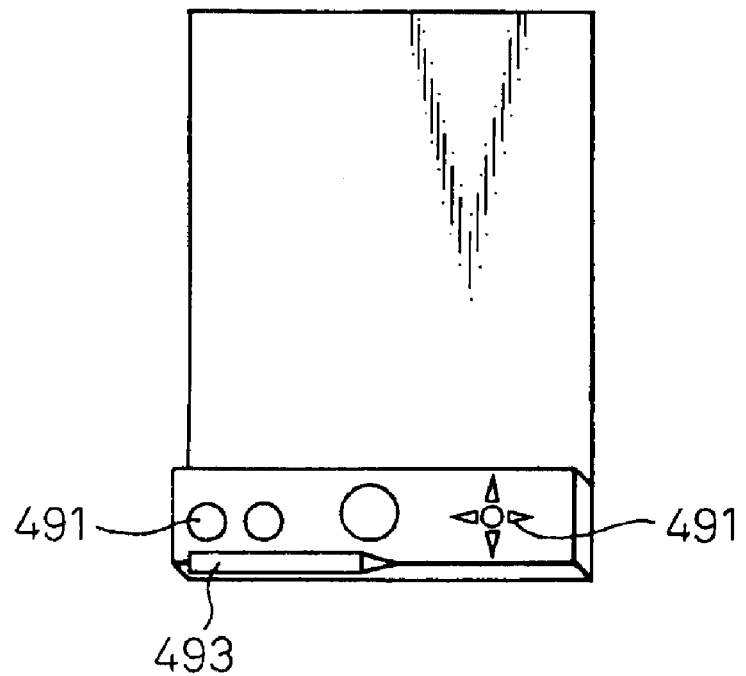
FIGS. 8A and 8B are views for explaining a communication tool as one embodiment of the sheet-form display device of the present invention.
Figure 8B:
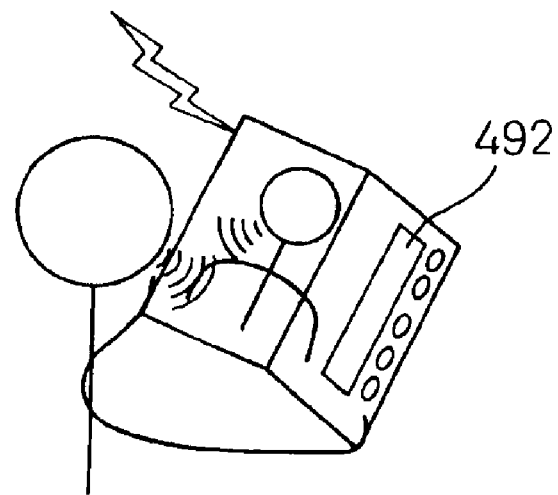

Examples of Application:

FIGS. 8A and 8B show the appearance. Using only the input using a key 491, communication can be made and conversation can be made while seeing the partner. The image information 492 from an image input means (not shown) such as camera or scanner can be input and sent. The display plane may be rolled in such a manner that the key input part is positioned in a center, a touch key (not shown) may be formed in a part of the display plane and, in the case where an input operation is not necessary, the key input part may be erased from the picture plane. The input may also be made by hand writing using an electronic pen 493.

(4) Electronic wallpaper system capable of freely changing color pattern or design by electric signal:

Examples of Form:

Lengthy form (for example, a width of 60 cm or more, a length of tens of meter or more), wallpaper-like thickness.

Examples of Function:

Renewal of image, etc.

Examples of Constituent Element:

Receiving, data memory, switchover of picture plane, input, etc.

Examples of Application:

FIG. 9 shows the appearance. The wallpaper part 501 is constructed of microcapsules having enclosed therein display particles (e.g., electrophoretic particles) and a display element comprising a common electrode and on the wall face 502, an individual electrode, a driving/control circuit, a power source and the like are provided. As such, the control circuit and the like are not integrated with the wallpaper part 501, so that the wallpaper can be cut at an arbitrary portion and made to function by attaching it on a wall. In this case, signals of an arbitrary display pattern can be input and displayed by a separately provided controlling device 503 (may be provided on a wall face 502). A power source is required only when the display pattern is changed, and no power source is necessary for holding the pattern. By earthing the surface, the attachment of dust or trash due to static electrification can be preserved and in turn contamination can be prevented. In the case of protecting the common electrode (not shown) of the wallpaper part 501, an electrically conducting resin or the like is thinly coated on the surface. According to the season or use end of the room, the pattern suitable for the situation can be selected and displayed. Not only the pattern of the wallpaper but also a picture or a photograph can be displayed and by displaying a window frame, the outdoor scene can be freely produced and displayed. Of course, the display can be applied to a ceiling. By reinforcing the protective layer and thereby imparting durability, the wallpaper can be used also as an outer wall surface and, according to the season, the color can be changed or the decoration for Christmas can be displayed. When a common electrode of the display element is provided in the wall surface side and connected to a control means, the pattern on the wallpaper surface can be changed using input means having also a driving circuit, such as writing stick.

(5) Large picture plane television fixed on wall:

Examples of Form:

About tens of inches or more, can be rolled up and can be removed.

Examples of Function:

Receiving (selection of channel, control), display, voice output, etc.

Examples of Constituent Element:

Display part, voice output (speaker), power source, communication (receiving), channel selection switch, etc.

Examples of Application:

The device can be moved to an arbitrary place and displayed by fixing it to a wall. Since lightweight, the device can be displayed by fixing it even to a ceiling or the like.

(6) Windable electronic conference document:

Examples of Form:

From A4 to A3 size (foldable into A4 size), thin like paper, a plurality of sheets may be superposed one on another and can be rolled up.

Examples of Function:

Receiving and sending, data memory, switchover of picture plane, enlargement/reduction, input, etc.

Examples of Constituent Element:

Display part, driving circuit, power source, communication (sending and receiving) circuit, control circuit, memory, input means, etc.

Examples of Application:

FIG. 10 shows the appearance. Several sheets are bound and a plurality of sheets are inserted to a binding member 511 constructed to contain a power source, a driving circuit, a control circuit, a memory and communication function means. The feeling of turning pages is realized, the information can be received by the communication and stored in a memory, and the necessary information can be retrieved on the display plane and displayed. Furthermore, this electronic conference document can be taken up around the binding member 511. The function and the construction are the same as those of the previously described electronic book or electronic catalogue. In addition thereto, by removing each display layer from the binding member (back cover part) 511, the document sheets can be compared by taking one by one with a hand or may be displayed by placing those side by side like paper on a desk or the like.

(7) Display apparatus of an electronic conference system which can perform a conference having a feeling of being at a conference room:

Examples of Form:

Several meters or more in length, rigidity of allowing gentle bending.

Examples of Function:

Receiving and sending, data memory, switchover of picture plane, input, voice and image input, etc.

Examples of Constituent Element:

Display part, driving circuit, power source, communication (sending and receiving) circuit, control circuit, memory, input means, voice input and output means, image input and output means, etc.

Figure 11:
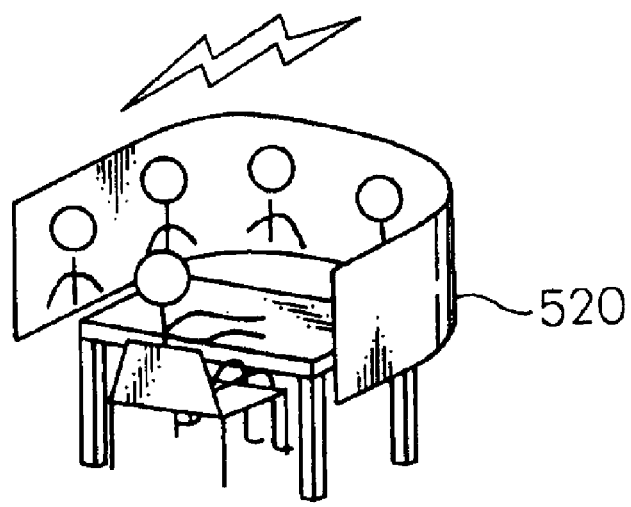
FIG. 11 is a view for explaining a display device for electronic conference system as one embodiment of the sheet-form display device of the present invention.

Examples of Application:

FIG. 11 shows the appearance of an electric conference system display device 520. Since the display can surround the conference attendance, the on-site feeling is elevated. The device is vertically placed to cover almost all of the visual field and a plurality of members are displayed on a large image plane by the image input means. The display can contain the positional relationship of partner members. The related data can be distributed by the communication and can be discussed by the conversation.

(8) Display device like paper, capable of being housed in writing too such as pen or being folded small:

(8-1) Display device capable being housed in pen, etc.:

Examples of Form:

About A6 size, can be rolled up.

Figure 12:
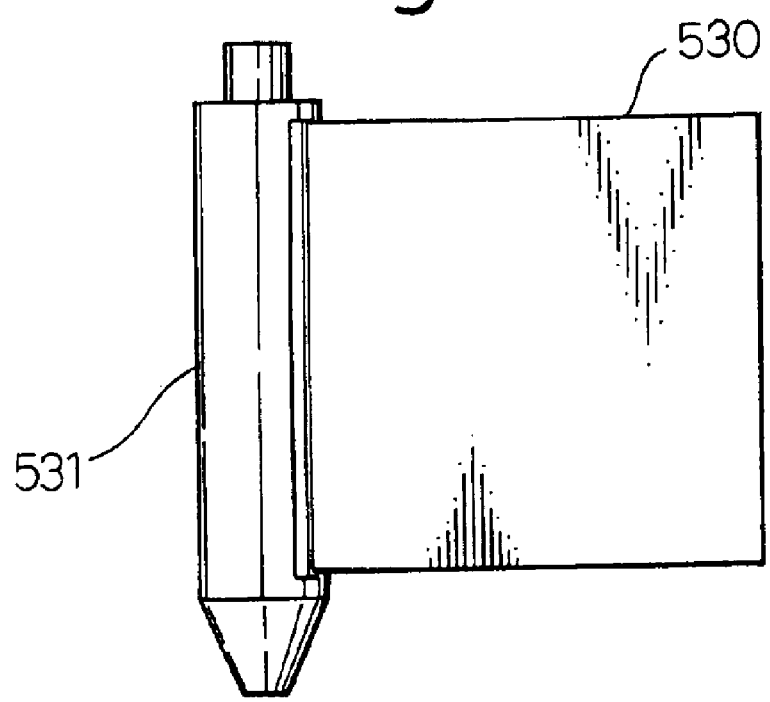
FIG. 12 is a view for explaining a display device capable of being housed in a pen as one embodiment of the sheet-form display device of the present invention.

Examples of Function:
　　Receiving, data memory, switchover of picture plane, etc.
Examples of Constituent Element:
　　Display part, driving circuit, power source, communication (receiving) circuit, control circuit, memory, input means, etc.
Examples of Application:
　　FIG. 12 shows an example of a display device 530 which is folded inside a pen 531. This display device 530 is in a form capable of being folded inside pen 531 and, on use, is appropriately pulled out. The device is connected at the edge with a driving circuit, a communication circuit, a control circuit, a power source (not shown) and the like provided inside the pen 531 and by these elements, information is received through an antenna (not shown) provided in the body of the pen 531, displayed and renewed. The image plane is controlled using a switch (not shown) provided in the body of the pen 531 or a touch key (not shown) provided on the display plane of the display device 530. Since the display device 530 is pulled out on use, this device preferably has a rigidity like a film sheet to facilitate handling.

(8-2) Small foldable display device:

Examples of Form:
　　From A4 to A3 size when unfolded, foldable into about A6 size.
Examples of Function:
　　Receiving, data memory, switchover of picture plane, etc.
Examples of Constituent Element:
　　Display part, driving circuit, power source, communication (receiving) circuit, control circuit, memory, input means, etc.
Examples of Application:
　　The same appearance as that of an electronic newspaper described in (1-1). A driving circuit, a communication circuit, a control circuit, a power source and the like are formed within the range of A6 as a final size when folded. This device can be folded like paper or rolled up and housed in a pocket. When necessary, the device can be taken out and unfolded to confirm the contents.

Figure 13A:
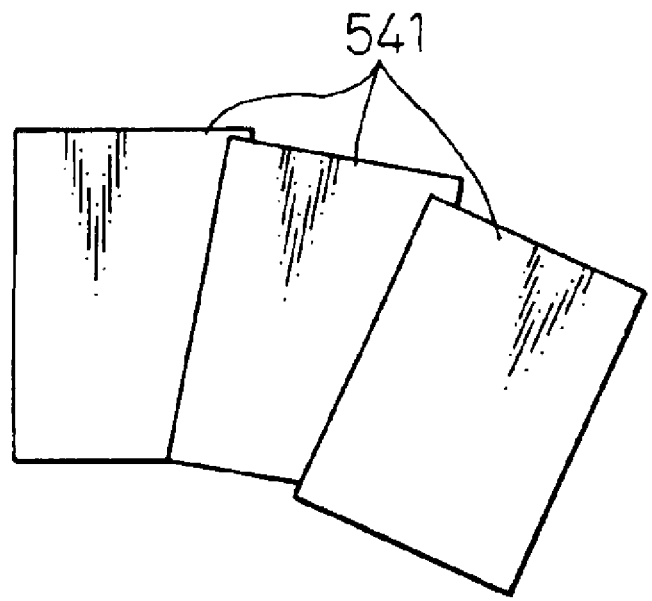
FIGS. 13A and 13B are views for explaining a paper-form display device as one embodiment of the sheet-form display device of the present invention.
Figure 13B:
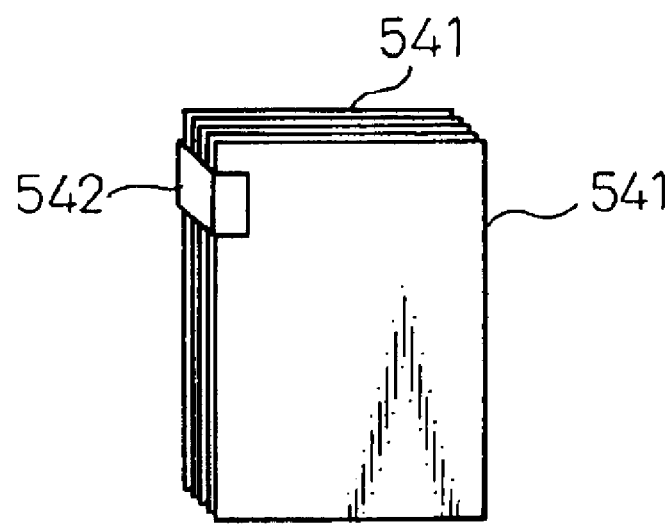

(9) Paper-form display device capable of being looked at by spreading many sheets on desk, being bound to store the information without power supply, and being erased or rewritten, if necessary:

Examples of Form:
　　From A4 to A3 size, having thickness and flexibility large enough to enable bending or folding.
Examples of Function:
　　Receiving and sending, data memory, switchover of picture plane, enlargement/reduction, input, etc.
Examples of Constituent Element:
　　Display part, driving circuit, power source, communication (sending and receiving) circuit, control circuit, memory, input means, etc.
Examples of Application:
　　FIG. 13A shows the appearance. As the display information can be held, it is possible to separate the driving part and use only the display part 541 like paper. Also, as shown in FIG. 13B, the device can be bound by means of a clip 542 or the like while holding the display information. In the case of renewing the display, as described in the electronic conference document of (6), the device is mounted on a binding member (back cover) (not shown) self-containing a control circuit and the like.

(10) Swinging poster hung in bus, electric car, etc., electronic poster, banner poster, POP poster each capable of renewing the display content by communication:

Examples of Form:
　　A3 size or more, flexibility of allowing rolling up, thin like paper.

Examples of Function:
　　Receiving and sending, data memory, switchover of picture plane, input, etc.
Examples of Constituent Element:
　　Display part, driving circuit, power source, communication (sending and receiving) circuit, control circuit, memory, input means, etc.
Examples of Application:
　　In addition to the automatic renewal of information by communication, a system such as a suspended poster enables acquisition of information, order for advertised commodity and settlement of account therefor through the connection with a potable information terminal of an individual person by means of communication or the like. In the electronic poster, POP poster and banner poster, the information of bargain sale or time service can be renewed in real time by the communication according to season, day, hour time, change or taste of customers, etc.. This device has input means capable of displaying or erasing and enables an order directly from the poster. In use of a banner poster, the information can be renewed by the communication once fixed and therefore, times or labors for exchanging the poster can be saved or danger in the exchanging work can be evaded.

Figure 14A:
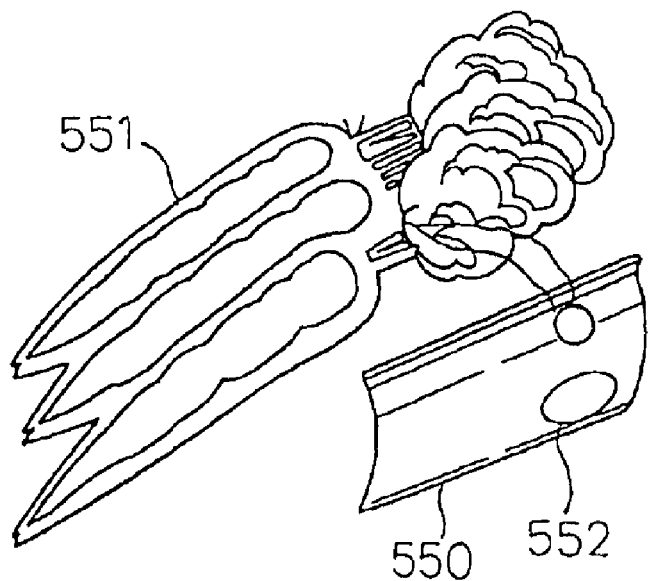
FIGS. 14A and 14B are views for explaining an electronic price tag as one embodiment of the sheet-form display device of the present invention.
Figure 14B:
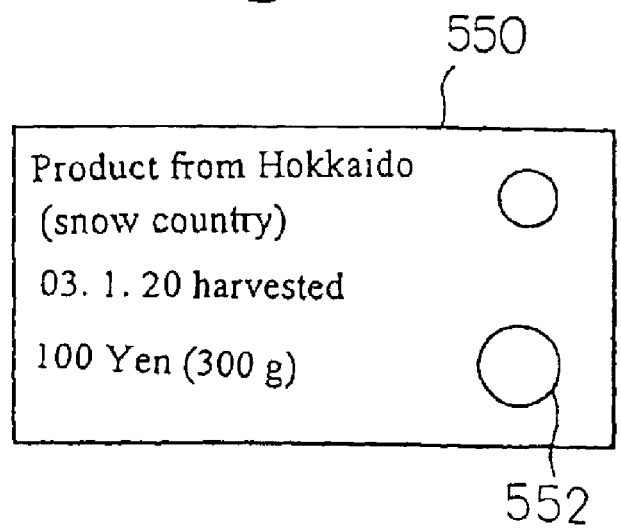

(11) Electronic price tag for food, displaying information such as production place or recipe:

Examples of Form:
　　About business card size, slightly bendable sheet form.
Examples of Function:
　　Display, memory, power source, receiving, data output.
Examples of Constituent Element:
　　Display part, driving circuit, power source, communication (sending and receiving) circuit, control circuit, memory, touch key, etc.
Examples of Application:
　　FIGS. 14a and 14B show the appearance of an electronic price tag. As shown in FIG. 14A, while fixing a price tag 550 on the commodity 551, the display can be rewritten by communication. As shown in FIG. 14B, commodity information such as product name, weight, price, production place, harvest day, acceptable eat time and product grade, a recipe using the commodity and the information of other food materials necessary for the recipe are displayed by operating a button 552 on the display surface and thereby switching over the information. The information as it is can be input into an information portable remote terminal and the information can be used for the management of a household economy or stock. Furthermore, consumers may bring it home, input the data into the information home appliance such as refrigerator and use it for stock management. The price tag after use is returned to the store and reused at the store by renewing the information or the like.

(12) Automatic payment system by electronic price tag, capable of settling account only by passing through gate:

Examples of Form:
　　About business card size, slightly bendable sheet form.
Examples of Function:
　　Display of sum, operation, communication (sending and receiving).
Examples of Constituent Element:
　　Display part, driving circuit, power source, communication (sending and receiving) circuit, control circuit, memory, touch key, etc.
Examples of Application:
　　A sending function is added to the electronic price tag of (11) above and the commodity information is sent in respondence to the access signal from the liquidation gate. The content transmitted is recorded and the account is settled by the direct debit from the previously registered account of a credit card or the like. Also, account details can be displayed on a separate sheet-form display device so that the purchaser can confirm.

(13) System capable of displaying price of commodity by electronic price tag, displaying total price or clearing account by putting commodity into shopping basket (or by taking it out):

Examples of Form:
 About business card size, slightly bendable sheet form.
Examples of Function:
 Display of sum, operation, communication (sending and receiving).
Examples of Constituent Element:
 Display part, driving circuit, power source, communication (sending and receiving) circuit, control circuit, memory, touch key, etc.
Examples of Application:
 A sending function is added to the electronic price tag described in (11) above, a display device capable of sending, receiving and operating is added also to the shopping basket, a signal is sent from commodity at the time of putting it into the shopping bag (or taken out from the shopping basket) and the price of commodity is automatically displayed in the display device of the basket. The total price is also displayed. In this system, upon establishment of the purchased commodity, the total price is confirmed and can be electrically settled.

(14) Seal-form warning display medium of urging caution only at opening of door of (at the getting on and off) vehicle such as electric car:

Examples of Form:
 From about A4 to A3 size, thin like paper, attachable/detachable on wall or the like.
Examples of Function
 Communication (receiving)
Examples of Constituent Element:
 Display part, driving circuit, power source, communication (receiving) circuit, control circuit, memory, etc.
Examples of Application:
 This device is attached in the vicinity of a door for entrance of a vehicle or on the door itself. The display shows a general guidance or an advertisement and is indistinguishable or shows nothing on running of the vehicle but, in response to the opening/closing of the door, a caution is displayed to call passengers' attention.

(15) Electronic newspaper and magazine having printed thereon poster or advertisement, capable of giving display or communication of detailed information by only touching a predetermined portion of the advertisement:

Examples of Form:
 From A4 to A3 size (foldable into A4 size), slightly bendable sheet form, removable (in the case of poster).
Examples of Function:
 Receiving and sending, data memory, switchover of picture plane, input.
Examples of Constituent Element:
 Display part, driving circuit, power source, communication (sending and receiving) circuit, control circuit, memory, input means, etc.
Examples of Application:
 A transparent touch sensor is provided on the surface and a touch key is not seen at the display time of advertisement but the position of touch key is displayed at the input time to enable input. The connection with a portable information remote terminal can be made by the communication and by inputting the information stored as a default at the terminal, and data or the like can be requested.

(16) Intelligent road and Traffic sign

Figure 15:
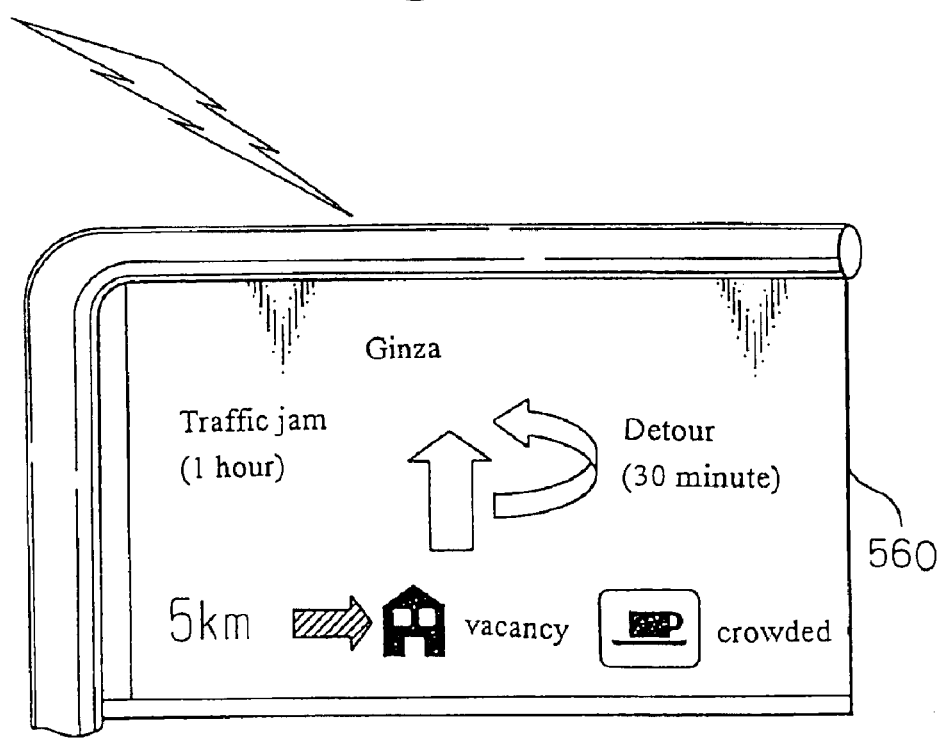
FIG. 15 is a view for explaining an intelligent road sign as one embodiment of the sheet-form display device of the present invention.

Examples of Form:
 One meter square or more, plate form.
Examples of Function:
 Receiving and sending, switchover of picture plane.
Examples of Constituent Element:
 Display part, driving circuit, power source, communication (sending and receiving) circuit, control circuit, memory, etc.
Examples of Application:
 FIG. 15 shows an example of a road sign. The information for road guide, including traffic jam information, bypass information, and reservation conditions of hotel or restaurant in the region is displayed and renewed in real time by communication. The display energy is small and energy is not necessary for holding the display. In the case of a traffic sign, the information on regulation can be automatically renewed according to the time. By adding a road monitoring function to the road sign or traffic sign, the information on traffic jam and the like can be automatically transmitted.

Figure 16A:
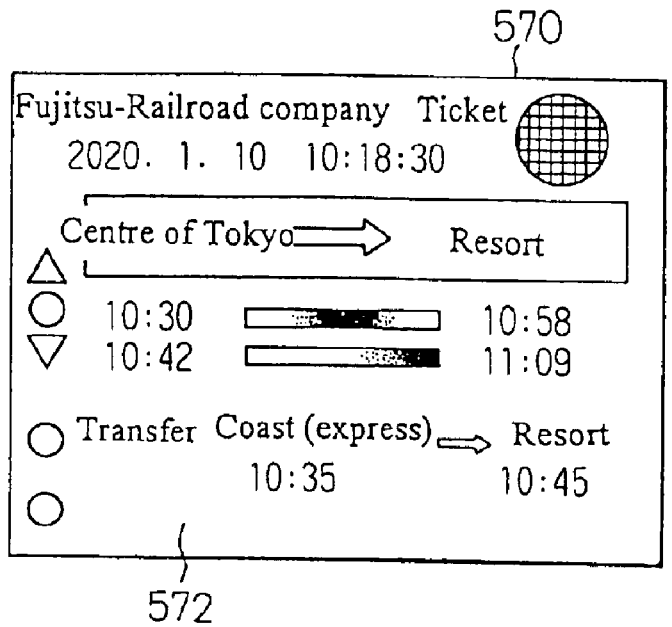
FIGS. 16A and 16B are views for explaining an intelligent electronic ticket as one embodiment of the sheet-form display device of the present invention.
Figure 16B:
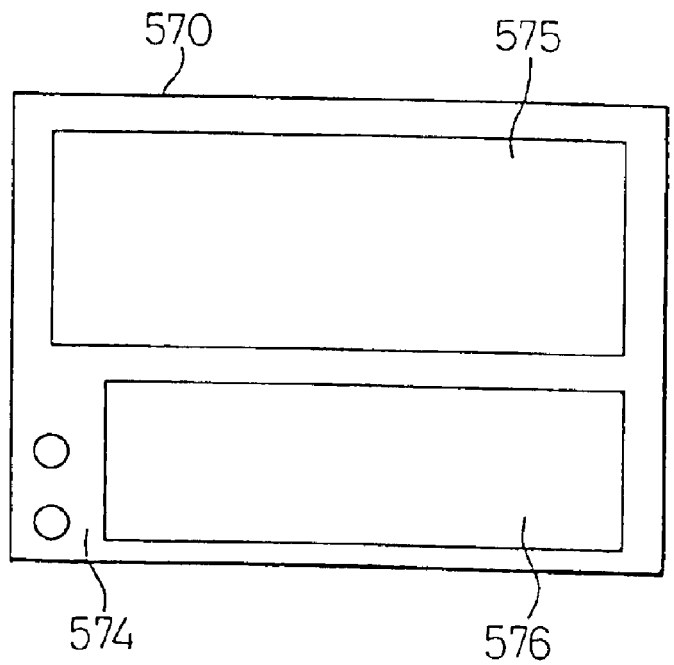

(17) Intelligent electronic ticket (railroad ticket, etc.) and commuter pass:

Examples of Form:
 Business card or commuter pass size, slightly rigid sheet form.
Examples of Function:
 Receiving and sending, data memory, switchover of picture plane, input, alarm, time display.
Examples of Constituent Element:
 Display part, driving circuit, power source, communication (sending and receiving) circuit, control circuit, memory, touch key, etc.
Examples of Application:
 FIGS. 16A and 16B show an example of an electronic ticket 570. In FIG. 16A, when the destination is selected at the time of purchasing the ticket, the surface 572 preferentially provides the information useful for the passenger other than the display of place to get on and off and fare which are originally not always necessary for the passenger. After the purchase of ticket, the entrance and ticket examination are completed by communication between the wicket gate and the ticket. This device also has a time display function and can display the departure time of trains on which the passenger can get after the hour at that time, the guidance of the departure platform, the arrival time at the destination, the service information such as crowding of each train car obtained by the communication function of ticket, and the information on changing of cars. These information items may be displayed at the same time or may be displayed by switching the picture plane using a switchover button such as a touch key. Furthermore, as the train comes near to the destination stored in memory, this is detected by the signal in place of announcement in the train or by the signal sent from the device disposed at stations on the way and notified to the passenger by an alarm (e.g., light, sound, vibration). Therefore, the announcement in the train is not necessary, as a result, not only comfortable environment is provided but also by selecting an alarm, convenient use is provided for (physically) handicapped passengers. On the back surface 574 shown in FIG. 16B, the display can also be made and the guidance 575 along the railroad line or an advertisement 576 can be displayed. According to the purpose of taking the train such as commutation or sight seeing, the kind of information displayed can be changed or in the case of commuter pass, the information desired by the passenger can be registered and displayed. At the time of exiting from the wicket, the ticket can communicate with the gate in the same manner as at the entrance and in the case of a general ticket, a system of inserting it into a ticket-examining machine and thereby performing the communication may be employed so as to recover the ticket without fail.

(18) Display device affixed to dashboard, incapable of being recognized at ordinary time but capable of displaying warning, information how to cope, etc. only at generation of abnormality:

Examples of Form:
About A4 size or less, thin like paper, removable.

Examples of Function:
Communication (receiving)

Examples of Constituent Element:
Display part, driving circuit, power source, communication (receiving) circuit, control circuit, memory, etc.

Examples of Application:
This device fundamentally realizes the same embodiment as the seal-form warning display medium of (14) and bears the same color as the dashboard at an ordinary time not to fine the fine appearance in the automobile, but only at the generation of troubles, display the optimal action or caution according to the trouble in respondence to the display signal of the trouble. By this, the oversight of display can be prevented, the recognition and comprehension of information can be enhanced, and a smooth and appropriate action can be taken.

(19) Electronic Text

Examples of Form:
From A4 to A3 size (foldable into A4 size), thin like paper, a plurality of sheets can be bound or rolled up.

Examples of Function:
Receiving and sending, data memory, switchover of picture plane, enlargement/reduction, input, search.

Examples of Constituent Element:
Display part, driving circuit, power source, communication (sending and receiving) circuit, control circuit, memory, input means, etc.

Examples of Application:
The fundamental construction is same as that of the electronic catalogue of (1-3) or the communication tool of (3). This device comprises a plurality of paper-form display elements having a function of, by communication, displaying information necessary for study, and searching for detailed information related to the studied matter, only by a button operation through an internet or the like, and displaying the information. In addition to the input means such as touch key capable of performing display or erasing on the display picture plane according to the use of a text, this device has a handwriting input function as in the electronic conference document of (6) and a note function for enabling storage of the input information.

(20) Display device for use in global education system and capable of displaying as if on paper:

Examples of Form:
A4 size or more.

Examples of Function:
Receiving and sending, data memory, switchover of picture plane, enlargement/reduction, input, search, image input, etc.

Examples of Constituent Element:
Display part, driving circuit, power source, communication (sending and receiving) circuit, control circuit, memory, input means, image input means, etc.

Figure 17:
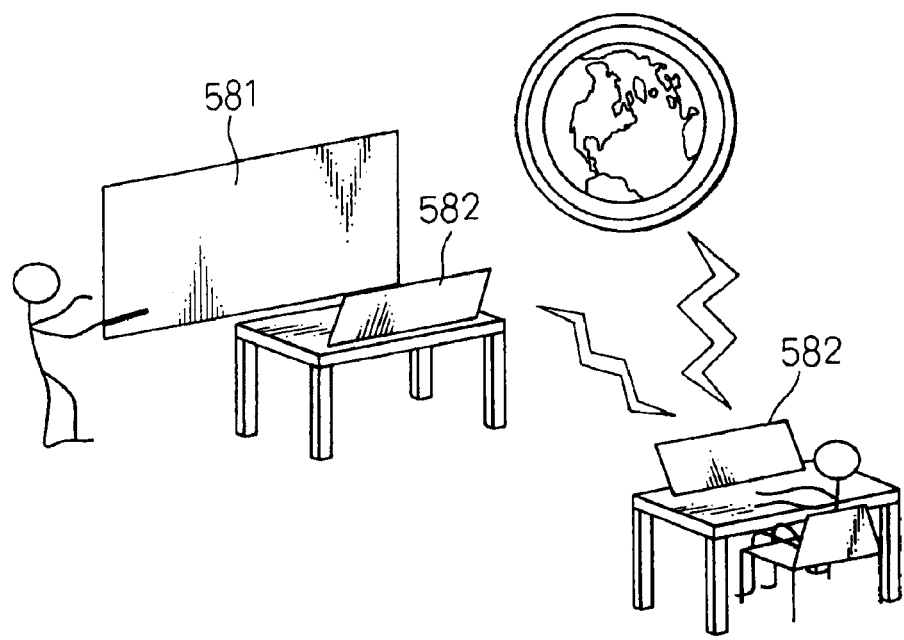
FIG. 17 is a view for explaining a display device for a global education system as one embodiment of the sheet-form display device of the present invention.

Examples of Application:
FIG. 17 shows an example of a display device for a global education system. The global education system as used herein includes an electronic blackboard 581 as the same display device as that of the electronic conference system of (7) and the same display device 582 as that of the electronic text of (19). By linking with schools around the world, the contents written on the electronic blackboard 581 by a teacher can be sent, displayed and recorded to the display device 582 of students. Individual communication between the teacher and a student can be supported. A voice input and output function and an image input function may also be added.

Figure 18:
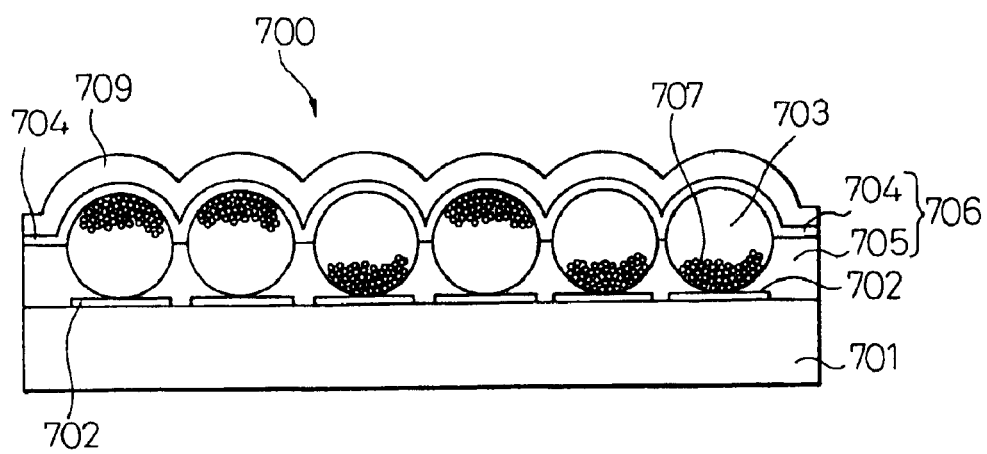
FIG. 18 is a view for explaining the sheet-form display device of the present invention, where a display layer and an electrode are integrally constructed.

A construction example of the sheet-form display device of the present invention using the electrically conducting resin layer as a common electrode positioned in the display surface side is described below by referring to FIG. 18.

As shown in the Figure, this sheet-form display device 700 has individual electrodes 702 formed on a substrate 701, microcapsules 703 each containing electrophoretic particles 707 and being disposed at respective positions corresponding to those individual electrodes 702 and fixed to the substrate 701 by an adhesive layer 705, and a common electrode 704 formed from the electrically conducting organic compound of the present invention and covering a display layer 706 composed of those microcapsules 703 and the adhesive layer 705. A pair of opposing electrodes are formed by those individual electrodes 702 and the common electrode 704. The common electrode 704 positioned in the display surface side of the display device 700 is usually transparent.

In the display device 700, the optical reflection or optical absorption of a microcapsule 703 is changed upon application of a potential difference between the counter electrodes 702 and 704 and thereby an image is displayed, where, as shown in FIG. 2, the electrode 704 in the display surface side is stacked on the display layer 706 and integrated therewith and, as a result, the obtained sheet-form display device can have a structure such that the thickness and the glossiness are close to those of paper. For integrating the common electrode 704 with the display layer 706, for example, a method of coating the electrically conducting resin material directly on the display layer 706 or a method of stacking a previously produced film (not shown) on the display layer 706 can be used.

Figure 19:
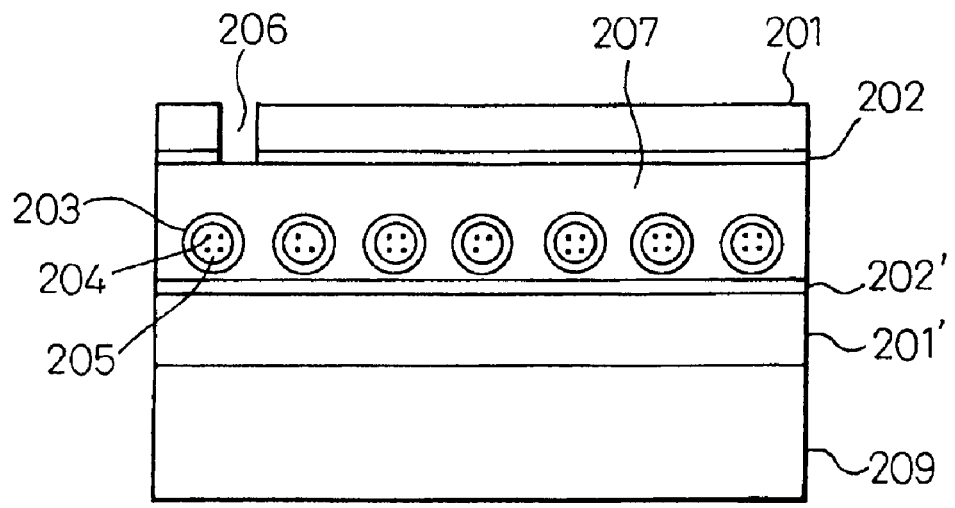
FIG. 19 is a view for explaining another embodiment of the sheet-form display device of the present invention.

A sheet-form display device having another construction and its production example are described below by referring to FIG. 19.

This sheet-form display device contains a display part and a power source part. The display part is constructed such that a large number of microcapsules 203 each enclosing a dispersion system 205 previously encapsulated by the microcapsulation process are interposed between a pair of transparent electrodes 202 and 202' formed on opposing surfaces (ITO vapor deposition surfaces) of transparent materials 201 and 201', respectively, where the dispersion system is prepared by dispersing electrophoretic particles in a dispersion medium and each transparent electrode comprises an ITO vapor deposition PET (polyethylene terephthalate) film. On one transparent material 201' on the side opposite the ITO deposition surface, an aluminum vapor deposition layer is formed. The electrically conducting organic compound of the present invention is used for the transparent electrodes 201 and 201'.

Examples of the electrophoretic particles 204 which can be used in the dispersion system 205 encapsulated in the microcapsule 203 include general colloid particles or metal fine particles, organic or inorganic dye, organic or inorganic pigment, ceramic or glass fine particles, and fine particles of appropriate resin or rubber. These particles may also be used in combination.

Examples of the dispersion medium which can be used in the dispersion system 205 include water, an aqueous solution of inorganic or organic salt, alcohols, amines, saturated or unsaturated hydrocarbons, halogenated hydrocarbons, naturally occurring fats and oils or mineral oils, and synthetic oils.

If desired, the dispersion system 205 may contain an inorganic or organic electrolyte, a surfactant or its salt, a charge controlling agent comprising particles of resin material or rubber, and a dispersant, a lubricant and a stabilizer each mainly including a surfactant system.

The dispersion system 205 is thoroughly mixed by a roll mill, a ball mill or the like and microencapsulated by the interfacial polymerization method or the coacervation method. The film for forming the outer periphery of the microcapsule 203 preferably has a volume resistivity equal to that of the dispersion system 205.

This microcapsule 203 is disposed on the surface of one transparent electrode 202' using a technique such as screen printing and enclosed between two electrodes by combining it with the other transparent electrode 202. For enclosing the dispersion system 205 between two electrodes 202 and 202' by means of the microcapsule 203, in addition to the above-described method, a technique of injecting a predetermined amount of microcapsules 203 using an inserting hole (not shown) communicating between two electrodes may also be used.

In practice, a substance 207 chemically stable against the microcapsule 203 and having a refractive index and a volume resistivity equivalent to those of the microcapsule is preferably filled into the space between microcapsules 203 and into the space between the electrode 202 or 202' and the microcapsule 203, through an injection hole 206 as shown in the Figure.

The manufacture of a battery 209 as the power source part is described below.

To 90 parts by mass of acetonitrile, 10 parts by mass of pyrrole is added and furthermore, 5 parts by mass of lithium tetrafluoroborate is added. These are uniformly mixed and then, 50 parts by mass of lithium cobaltate is added. The mixture is gently stirring and left standing for 10 minutes. The lithium cobaltate is separated by filtration, washed with acetonitrile and dried at 80° C. for 10 minutes. To 100 parts by mass of the obtained powder, 3 parts by mass of acetylene black is added and mixed in a mill. Thereafter, the obtained powder particles are mixed and kneaded with 50 parts by mass of a 10% N-methylpyrrolidone solution of polyvinylidene fluoride and the resulting paste is coated on the vapor deposition aluminum surface of the transparent 201' in the display part to a thickness of 150 $\mu$m and dried at 120° C. for 30 minutes to prepare a positive electrode foil.

The solid electrolyte used is an acryl-modified polyethylene oxide. 100 parts by mass of a 10:1 mixture of end acryl-modified polyethylene oxide and both ends acryl-modified polyethylene oxide, and 100 parts by mass of propylene carbonate containing 1M lithium tetrafluoroborate are mixed, and thereto, 1 part by mass of benzoyl peroxide is further added to prepare a reaction polymerization solution.

On the positive electrode prepared above, a 40 $\mu$m-thick non-fabric is placed, the reaction polymerization solution of solid electrolyte is cast to a film thickness of 100 $\mu$m, and then ultraviolet light (1 mW/cm$^2$) of an extra-high pressure mercury lamp is irradiated thereon for 1 minute to perform the polymerization, thereby forming a solid electrolyte film in a gel state.

On the other hand, 1 part by mass of a 10% N-methylpyrrolidone solution of polyvinylidene fluoride is mixed and kneaded with 1 part by mass of graphite-type carbon and the paste obtained is coated on a negative electrode collector (10 $\mu$m-thick copper foil) to a thickness of 100 $\mu$m and dried at 120° C. for 30 minutes to produce a negative electrode. This negative electrode is placed on the above-described half battery having formed thereon an electrolyte and a pressure of 2 kg/cm$^2$ (196 kPa) is applied to complete the battery. The voltages of the positive and negative electrodes can be obtained through the collectors having supported thereon the respective corresponding electroactive materials.

In this way, a sheet-form display device having a display device and a secondary battery integrated with each other and having a display function can be obtained.

EXAMPLES

The present invention is described in greater detail by referring to the Examples. It should be understood that the present invention is not limited to the following Examples.

Example 1

On a substrate plastic sheet comprising polyether sulfone, a gate electrode was formed by sputtering of gold, cyanoethylated pullulan dissolved in acetone was coated thereon, and then the solvent was dried to form an insulating layer having a film thickness of 150 nm. On this insulating layer, a source electrode and a drain electrode at an electrode-to-electrode distance, namely, a channel length, of 5 $\mu$m were each formed to a film thickness of 50 nm by sputtering of gold. On the plastic substrate with electrodes thus formed, an ovalene derivative having attached thereto a hexyl group (see, the following formula):

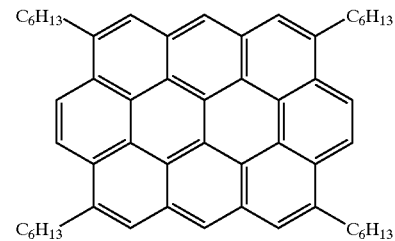

which was dissolved under heating in toluene was coated by spin coating and then, the solvent was gradually dried to obtain a channel layer having a film thickness of 100 nm.

Subsequently, for the thus-manufactured organic thin film transistor, the mobility of the electrically conducting organic compound was calculated from the relationships between the drain voltage and the drain current and between the gate voltage and the drain current. The mobility was maximally $\mu$=0.01 cm$^2$/Vs at room temperature.

Example 2

On a substrate plastic sheet comprising polyether sulfone, a gate electrode was formed by sputtering of gold and patterning, cyanoethylated pullulan dissolved in acetone was coated thereon, and then the solvent was dried to form an insulating layer having a film thickness of 150 nm. On this insulating layer, a source electrode and a drain electrode at an electrode-to-electrode distance, namely, a channel length, of 5 μm were formed each to a film thickness of 50 nm by sputtering of gold.

On the plastic substrate with electrodes thus formed, a bianthrene derivative having attached thereto a hexyl group (see, the following formula):

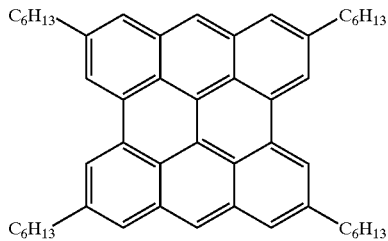

which was dissolved under heating in toluene was coated by spin coating and then, the solvent was gradually dried while applying an electric field between the source-drain electrodes to obtain a channel layer having a film thickness of 100 nm.

Subsequently, for thus-manufactured organic thin film transistor, the mobility of the electrically conducting organic compound was calculated from the relationships between the drain voltage and the drain current and between the gate voltage and the drain current. The mobility was maximally $\mu=0.004$ cm$^2$/Vs at room temperature.

Example 3

On a substrate plastic sheet comprising polyether sulfone, a gate electrode was formed by sputtering of gold and patterning, cyanoethylated pullulan dissolved in acetone was coated thereon, and then the solvent was dried to form an insulating layer having a film thickness of 150 nm. On this insulating layer, a source electrode and a drain electrode at an electrode-to-electrode distance, namely, a channel length, of 5 μm were formed each to a film thickness of 50 nm by sputtering of gold. On the plastic substance with electrodes thus formed, an ovalene derivative having attached thereto a hexyl group (see, the following formula):

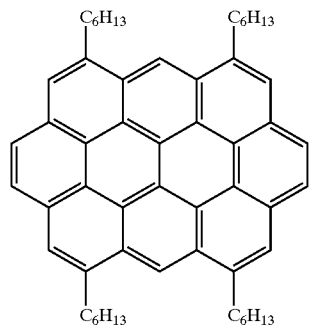

which was dissolved under heating in toluene was coated by spin coating and then, the solvent was gradually dried to obtain a channel layer having a film thickness of 100 nm.

Subsequently, for the thus-manufactured organic thin film transistor, the mobility of the electrically conducting organic compound was calculated from the relationships between the drain voltage and the drain current and between the gate voltage and the drain current. The mobility was maximally $\mu=0.0015$ cm$^2$/Vs at room temperature.

Comparative Example 1

The procedure described in Example 2 was repeated except that in this Comparative Example, the gate electrode was formed by etching of ITO in place of gold and the channel layer was formed by vacuum deposition in place of spin coating, more specifically, an unsubstituted bianthrene (see, following formula):

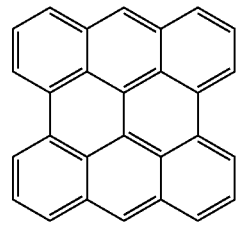

was formed in a vacuum under a pressure of about $1\times10^{-4}$ Pa at a film formation speed of 0.5 Å/s to obtain a channel layer having a film thickness of 100 nm.

Subsequently, for the thus-manufactured organic thin film transistor, the mobility of the electrically conducting organic compound was calculated from the relationships between the drain voltage and the drain current and between the gate voltage and the drain current. The mobility was maximally $\mu=0.0001$ cm$^2$/Vs at room temperature.

According to the present invention, a functional group capable of solubilizing in a solvent is introduced into ovalene, bianthrene and the like having a molecular skeleton with a π-conjugate system being planarly extended, whereby a thin film can be formed from a solution system by an easy film formation method such as coating or printing. The obtained organic semiconductor material can be improved in the field effect mobility as compared with conventional techniques for an organic semiconductor material manufactured from a solution system and at the same time, can contribute to the simplification and cost reduction of the production process of electronic devices such as field effect transistors. In particular, according to the present invention, a mobility as high as about two figures or orders in number in comparison with conventional techniques can be achieved and this in turn contributes to elevation in the operation rate of an organic thin film transistor and the like. Furthermore, according to the present invention, a flexible plastic substrate can be used and, therefore, electronic paper and the like, which has attracted attention in recent years, can be easily realized.

What is claimed is:

1. An electronic device comprising, as one member thereof, a constituent element formed from the electrically conducting organic compound, in which said organic compound is an ovalene derivative represented by the following formula (I):

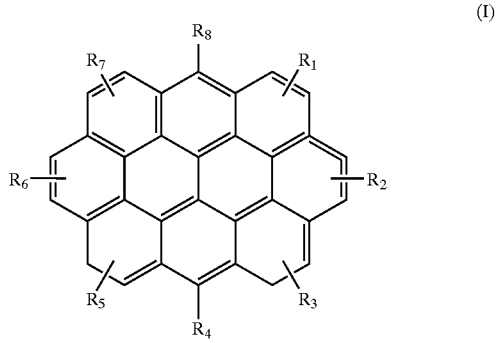

(I)

wherein $R_1$ to $R_8$, which may be the same or different, each represents hydrogen atom on an arbitrary substituent, provided that at least two of $R_1$ to $R_8$ are a silane group; or a bianthrene derivative represented by the following formula (II):

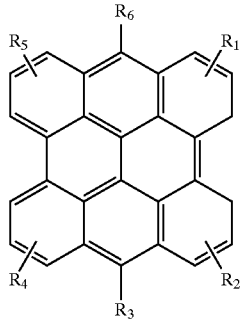

(II)

wherein $R_1$ to $R_6$, which may be the same or different, each represents a hydrogen atom or an arbitrary substituent, provided that at least two $R_1$ to $R_5$ are a silane group.

2. The electronic device as defined in claim 1, in which said organic compound has a field effect mobility of 0.001 cm$^2$/Vs or more.

3. The electronic device as defined in claim 1, in which said organic compound has a molecular weight of from 100 to 2,000.

4. An electronic device comprising, as one member thereof, a constituent element formed from the electronically conducting organic compound, in which said organic compound is an ovalene derivative represented by the following formula:

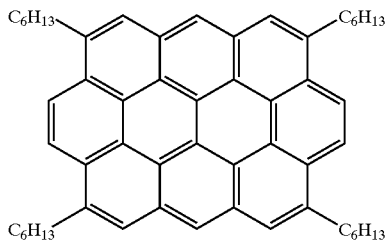

or

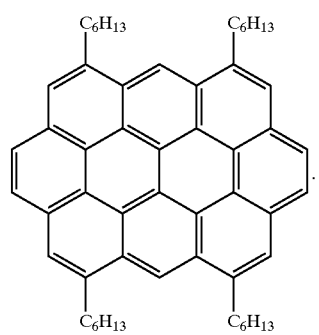

5. An electronic device comprising, as one member thereof, a constituent element formed from the electrically conducting organic compound, in which said organic compound is a bianthrene derivative represented by the following formula:

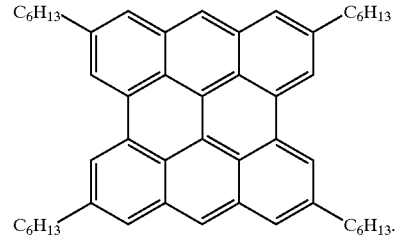

6. An electronic device in an organic thin film transistor comprising a substrate having thereon a gate electrode, a gate insulator, a source electrode, a drain electrode and a channel layer, the channel layer being formed of an electrically conducting organic compound, in which said organic compound is an ovalene derivative represented by the following formula (I):

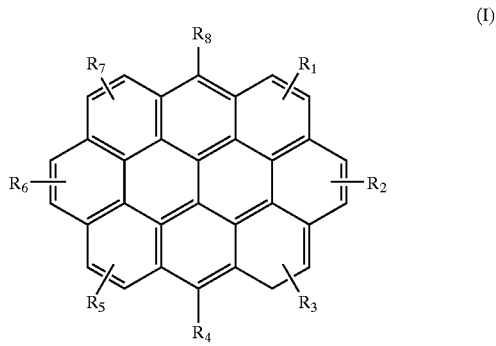

(I)

wherein $R_1$ to $R_6$, which may be the same or different, each represents a hydrogen atom or an arbitrary substituent, provided that at least two of $R_1$ to $R_8$ are a silane group; or a bianthrene derivative represented by the following formula (II);

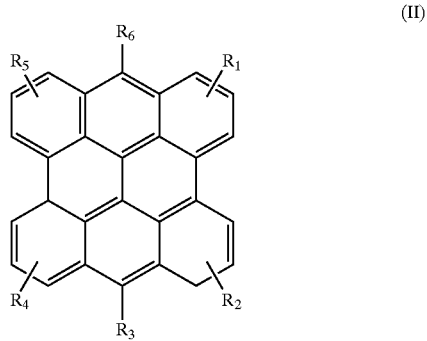

(II)

wherein $R_1$ to $R_6$, which may be the same or different, each represents a hydrogen atom or an arbitrary substituent, provided that at least two of $R_1$ to $R_6$ are a silane group.

7. The electronic device as defined in claim 6, wherein the substrate comprises a plastic material.

8. The electronic device as defined in claim 1 or 6, wherein the constituent element is formed by dissolving said electrically conducting organic compound in a solvent.

9. The electronic device as defined in claim 8, wherein the constituent element is formed by coating and curing a solution of said electrically conducting organic compound.

10. The electronic device as defined in claim 8, wherein the constituent element is formed by printing and curing a solution of the electrically conducting organic compound.

11. The electronic device as defined in claim 1 or 6, which has flexibility and is foldable.

12. The electronic device as defined in claim 1 or 6, which is in the form of electronic paper.

* * * * *